United States Patent [19]
Komari et al.

[11] Patent Number: 5,731,179
[45] Date of Patent: Mar. 24, 1998

[54] METHOD FOR INTRODUCING TWO T-DNAS INTO PLANTS AND VECTORS THEREFOR

[75] Inventors: Toshihiko Komari; Yasuhito Saito; Yukoh Hiei, all of Iwata-gun, Japan

[73] Assignee: Japan Tobacco Inc., Tokyo, Japan

[21] Appl. No.: 500,952

[22] PCT Filed: Dec. 6, 1994

[86] PCT No.: PCT/JP94/02049

§ 371 Date: Aug. 8, 1995

§ 102(e) Date: Aug. 8, 1995

[87] PCT Pub. No.: WO95/16031

PCT Pub. Date: Jun. 15, 1995

[30] Foreign Application Priority Data

Dec. 8, 1993 [JP] Japan ................................ 5-340657

[51] Int. Cl.$^6$ .................. C12N 15/05; C12N 15/84; C12N 1/20; A01H 5/00
[52] U.S. Cl. ................. 435/172.3; 435/252.2; 435/252.3; 435/252.33; 435/320.1; 800/205
[58] Field of Search ............... 435/252.33, 172–3, 435/320.1, 252.2, 252.3; 800/205

[56] References Cited

U.S. PATENT DOCUMENTS

| | | | |
|---|---|---|---|
| 5,149,645 | 9/1992 | Hoekema et al. | 435/172.3 |
| 5,164,310 | 11/1992 | Smith et al. | 435/172.3 |
| 5,177,010 | 1/1993 | Goldman et al. | 435/172.3 |
| 5,187,073 | 2/1993 | Goldman et al. | 435/172.3 |

FOREIGN PATENT DOCUMENTS

| | | |
|---|---|---|
| 0290799 | 11/1988 | European Pat. Off. . |
| 0320500 | 6/1989 | European Pat. Off. . |
| 0116718 | 5/1990 | European Pat. Off. . |
| 0159418 | 5/1990 | European Pat. Off. . |
| 0120516 | 10/1991 | European Pat. Off. . |
| 0504869 | 9/1992 | European Pat. Off. . |
| 4-222527 | 8/1992 | Japan . |
| WO 94/00977 | 1/1994 | WIPO . |
| WO 95/06722 | 3/1995 | WIPO . |

OTHER PUBLICATIONS

An et al. New cloning vehicles for transformation of higher plants. The EMBO Journal, 4(2):277–284, 1985.
Komari, T. Transformation of cultured cells of Chenopodium quinoa by binary vectors that carry a fragment of DNA from the virulence region of pTiBo542. Plant Cell Reports 9:303–306, 1990.
De Block et al., Theor. Appl. Genet. (Jan. 23, 1991): 82:257–263.
"Plant Molecular Biology Manual", Edited by: Stanton B. Gelvin and Robert A. Schilperoort, Kluwer Academic Publishers (1988).
Bevan et al, Nature, vol. 304, pp. 184–187 (Jul. 14, 1983).
Depicker et al., Mol. Gen. Genet., 201:477–484 (1985).
Hoekema et al., Nature, vol. 303, pp. 179–180 (May 12, 1983).
Jefferson, Plant Molecular Biology Reporter, vol. 5, No. 4, pp. 387–405 (1987).
Knauf et al, Plasmid, vol. 8, pp. 45–54 (1982).
Herrera–Estrella et al, The EMBO Journal, vol. 2, No. 6, pp. 987–995 (1983).
Hood et al, Biotechnology, vol. 2, pp. 702–709 (1984).
Hood et al, Journal of Bacteriology, vol. 168, No. 3, pp. 1283–1290 (Dec. 1986).
Shimamoto et al, Nature, vol. 338, pp. 274–277 (Mar. 16, 1989).
Jin et al, Journal of Bacteriology, vol. 169, No. 10, pp. 4417–4425 (Oct. 1987).
Komari, Plant Science, vol. 60, pp. 223–229 (1989).
Komari et al, Journal of Bacteriology, vol. 166, No. 1, pp. 88–94 (Apr. 1986).
De Greve et al, Plasmid, vol. 6, pp. 235–248 (1981).
Ditta et al, Proc. Natl. Acad. Sci. U.S.A., vol. 77, No. 12, pp. 7347–7351 (Dec. 1980).
Ohta et al, Plant Cell Physiol., 31(6), pp. 805–81 (1990).
Toriyama et al, Plant Science, vol. 41, pp. 179–183 (1985).
Pietrzak et al, Nucleic Acids Research, vol. 14, No. 14, pp. 5857–5868 (1986).
Gritz et al, Gene, vol. 25, pp. 179–188 (1983).
Murashige et al, Physiol. Plant, vol. 15, pp. 473–497 (1962).

(List continued on next page.)

*Primary Examiner*—Douglas W. Robinson
*Assistant Examiner*—Thanda Wai
*Attorney, Agent, or Firm*—Birch, Stewart, Kolasch & Birch, LLP

[57] ABSTRACT

The invention provides a method for transforming a plant through a bacterium belonging to genus Agrobacterium, comprising transforming plant cells simultaneously with a first T-DNA (1) and a second T-DNA (2); and selecting the cells which acquired drug resistance; the first T-DNA (1) containing a gene giving the drug resistance, which functions in the plant; the second T-DNA (2) containing a desired DNA fragment to be introduced into the plant, the second T-DNA (2) being contained in a hybrid vector; the hybrid vector being prepared by homologous recombination between an acceptor vector and an intermediate vector in the bacterium belonging to genus Agrobacterium; the acceptor vector containing at least (a) a DNA region having a function to replicate a plasmid in the bacterium belonging to genus Agrobacterium and *Escherichia coli*, (b) a DNA region containing virB gene and virG gene in virulence region of Ti plasmid pTiBo542 of *Agrobacterium tumefaciens*, and (c) a DNA region which is homologous with a part of the intermediate vector, which is subjected to homologous recombination in the bacterium belonging to genus Agrobacterium; the intermediate vector containing at least (i) a DNA region having a function to replicate a plasmid in *Escherichia coli*, which does not function in the bacterium belonging to genus Agrobacterium, (ii) a DNA region which is homologous with a part of the acceptor vector, which is subjected to homologous recombination in the bacterium belonging to genus Agrobacterium, and (iii) a DNA region which constitutes at least a part of the second T-DNA.

25 Claims, 14 Drawing Sheets

OTHER PUBLICATIONS

Chih–ching, Plant Tissue Culture, pp. 43–51 (1978).
Chilton et al, Proc. Natl. Acad. Sci. U.S.A., vol. 71, No. 9, pp. 3672–3676 (Sep. 1974).
An, Plant Physiol., vol. 81, pp. 86–91 (1986).
Horsch et al, Science, vol. 223, pp. 496–499 (Feb. 3, 1984).
McKnight et al, Plant Molecular Biology, vol. 8, pp. 439–445 (1987).

de Framond et al, Mol. Gen. Genet., 202:125–131 (1986).

Komari, Plant Cell Reports, 9:303–306 (1990).

Fraley et al, Proc. Natl. Acad. Sci. U.S.A., vol. 80, pp. 4803–4807 (Aug. 1983).

Hiei et al, The Plant Journal, vol. 6, No. 2, pp. 271–282 (1994).

METHOD FOR INTRODUCING TWO T-DNAS INTO PLANTS AND VECTORS THEREFOR

This application is a 371 of PCT/JP94/02049, filed Dec. 6, 1994.

TECHNICAL FIELD

The present invention relates to a method for transforming plants and a vector therefor.

BACKGROUND ART

Methods for introducing foreign genes (methods for transformation) to higher plants are largely classified into direct introduction methods and methods through bacteria belonging to the genus Agrobacterium. The former includes methods in which electric stimulation is utilized (electroporation method and electroinjection method); methods in which chemical treatments such as treatment with PEG are performed; and methods in which a particle gun is employed. The former is widely used for transforming monocotyledons to which the latter method is hardly applied. The latter is the methods in which the abilities of bacteria belonging to the genus Agrobacterium such as *Agrobacterium tumefaciens* and *A. rhizogenes* for transforming higher plants are utilized. The latter methods are excellent methods by which DNA fragments having relatively large sizes and having definite ends can be effectively introduced into higher plants, which do not require special culturing techniques such as protoplasts-culturing technique.

Methods for transformation are indispensable to studies of genetic engineering and molecular biology of higher plants, and a method by which a given DNA fragment is efficiently introduced into plant cells and by which a plant containing the DNA fragment is efficiently obtained is demanded. In introduction of a gene, it is necessary to select the plant cells into which the foreign gene is introduced from the plant cells into which the foreign gene is not introduced. Usually, since the number of the latter cells are much larger, it is necessary to utilize a gene which can be easily detected. The most widely used selection markers are drug resistant genes. Examples thereof include antibiotics resistant genes such as kanamycin resistant gene and hygromycin resistant gene; and herbicide resistant genes such as Basta resistant gene and Roundup resistant gene.

In cases where a drug resistance gene is used as a selection marker, a DNA fragment of interest to be introduced into a plant and the drug resistance gene are connected, the connected genes are introduced into plants, drug resistant cells are selected and transformed plants are obtained from the drug resistant cells. In the transformed plants thus obtained, the DNA fragment of interest connected to the drug resistance gene is also simultaneously introduced.

However, this method has the following two problems:

1. Despite the fact that the selection marker is necessary only in introduction of the gene, the selection marker always accompanies the introduced DNA fragment of interest during the subsequent growing step and even in the plants of subsequent generations. Thus, transformed plants containing the unnecessary gene are obtained. In cases where the transformation method is employed in breeding of crops, since varieties which do not contain such an unnecessary gene will have better reputation, the existence of the unnecessary gene is a big problem. Further, when another DNA fragment is introduced into the transformed plants, it is necessary to use another selection marker, which is inconvenient. This is also a big problem.

2. Since the operation to connect the selection marker and the DNA fragment of interest to be introduced into the plant is necessary, one additional step is required in construction of the gene to be introduced.

To avoid these problems, in the direct introduction methods, so called co-transformation method has been developed and widely used (Shimamoto et al., Nature 338:274–276, 1989). In this method, the DNA of the drug resistance gene as a selection marker and a DNA fragment of interest to be introduced into plants are merely mixed without ligation and the mixture is introduced into the plants. In the plants selected according to the drug resistance, some plants contain both the drug resistance gene and the DNA fragment of interest to be introduced into the plants. By controlling the mixing ratio of the two types of DNA, more often than not, the percentage of the drug resistant plants which contain the two types of DNA is not less than 50%.

Since the two types of DNA fragments thus introduced are not ligated, they may be independently inherited and segregated in the next generation. Therefore, in the next generation, transformed plants which contain the introduced DNA fragment of interest without containing the selection marker can be obtained.

The DNA fragment introduced into plants by bacteria belonging to the genus Agrobacterium is usually called T-DNA (transfer DNA) which is characterized by having repeating sequences at both ends thereof, that are called right border and left border, respectively. An artificial DNA fragment constituted by the left and right border sequences and a DNA of interest may also be called a T-DNA. A number of wild type bacteria belonging to the genus Agrobacterium contain two types of T-DNA, and plant cells transformed with such bacteria contain the two types of T-DNA, so that the phenomenon of co-transformation per se is known for a long time.

However, introduction of two types of T-DNA is not mentioned in the fundamental technique of the transformation method through Agrobacterium bacteria (Japanese Laid-open Patent Application (Kokai) No. 60-70080; Japanese Patent Publication (Kokoku) No. 2-58917; Herrera-Estrella et al., The EMBO Journal 6:987–995, 1983; Bevan et al., Nature 304:184–187, 1983; Fraley et al., Proc. Natl. Acad. Sci, U.S.A. 80:4803–4807, 1983) and in the improved highly efficient transformation technique Komari, Plant Cell Reports 9:303–306, 1990).

Simultaneous introduction of two types of T-DNA includes:

1. cases in which a first T-DNA and a second T-DNA are contained in the same Agrobacterium bacterial cell; and
2. cases in which the first T-DNA and the second T-DNA are contained in different Agrobacterium bacterial cells and a mixture of the two types of Agrobacterium bacterial cells is used.

It was shown that in either case, the two types of T-DNA transformed into plants independently inherited and segregated in the next generation (Depicker et al., Mol. Gen. Genet. 201:477–484, 1985; de Framond et al., Mol. Gen. Genet. 202:125–131, 1986; McKnight et al., Plant Molecular Biology 8:439–445, 1987).

However, in these conventional techniques, the efficiency to obtain regenerated plants into which both of the two types of T-DNA are introduced is low. Therefore, co-transformation through Agrobacterium bacteria is not widely employed.

DISCLOSURE OF THE INVENTION

An object of the present invention is to provide a method for transforming a plant by which regenerated transformed plant having a desired gene introduced can be prepared with a high efficiency, which enables to obtain a transformed plant in the next generation that contains the desired gene but does not contain the selection marker utilized such as a drug resistance gene.

The present inventors intensively studied to discover that the above-mentioned object may be attained by introducing by co-transformation into higher plants a first T-DNA containing a drug resistant gene and a second T-DNA into which a DNA fragment of interest to be introduced into the plant is inserted.

That is, the present invention provides a method for transforming a plant through a bacterium belonging to the genus Agrobacterium, comprising co-transforming plant cells with a first T-DNA (1) and a second T-DNA (2); and selecting the cells which acquired drug resistance;

the first T-DNA (1) containing a gene giving the drug resistance, which functions in the plant;

the second T-DNA (2) containing a desired DNA fragment to be introduced into the plant, the second T-DNA (2) being contained in a hybrid vector;

the hybrid vector being prepared by homologous recombination between an acceptor vector and an intermediate vector in the bacterium belonging to genus Agrobacterium;

the acceptor vector containing at least (a) a DNA region having a replication origin allowing replication of a plasmid in both a bacterium belonging to the genus Agrobacterium and in *Escherichia coli*, (b) a DNA region containing virB gene and virG gene in virulence region of Ti plasmid pTiBo542 of *Agrobacterium tumefaciens*, and (c) a DNA region which is homologous with a part of the intermediate vector, which is subjected to homologous recombination in the bacterium belonging to the genus Agrobacterium;

the intermediate vector containing at least (i) a DNA region having a replication original allowing replication of a plasmid in *Escherichia coli*, which does not function in the bacterium belonging to the genus Agrobacterium, (ii) a DNA region which is homologous with a part of the acceptor vector, which is subjected to homologous recombination in the bacterium belonging to the genus Agrobacterium, and (iii) a DNA region which constitutes at least a part of the second T-DNA.

The present invention also provides a hybrid vector comprising a first T-DNA containing (1) a selection marker gene such as a gene giving drug resistance, which functions in a plant, and (2) a second T-DNA having a restriction site;

the hybrid vector being prepared by homologous recombination between an acceptor vector and an intermediate vector in a bacterium belonging to the genus Agrobacterium;

the acceptor vector containing at least (a) a DNA region having a replication origin allowing replication of a plasmid in the bacterium belonging to the genus Agrobacterium and *Escherichia coli*, (b) a DNA region containing virB gene and virG gene in virulence region of Ti plasmid pTiBo542 of *Agrobacterium tumefaciens*, and (c) a DNA region which is homologous with a part of the intermediate vector, which is subjected to homologous recombination in the bacterium belonging to the genus Agrobacterium;

the intermediate vector containing at least (i) a DNA region having a replication origin allowing replication of a plasmid in *Escherichia coli*, which does not function in the bacterium belonging to the genus Agrobacterium, (ii) a DNA region which is homologous with a part of the acceptor vector, which is subjected to homologous recombination in the bacterium belonging to the genus Agrobacterium, and (iii) a DNA region which constitutes at least a part of the second T-DNA.

By the present invention, regenerated transformed plants having a desired gene introduced can be prepared with a high efficiency, and transformed plants in the next generation that contain the desired gene but do not contain the selection marker such as a drug resistant gene utilized can be obtained.

Figure 1:
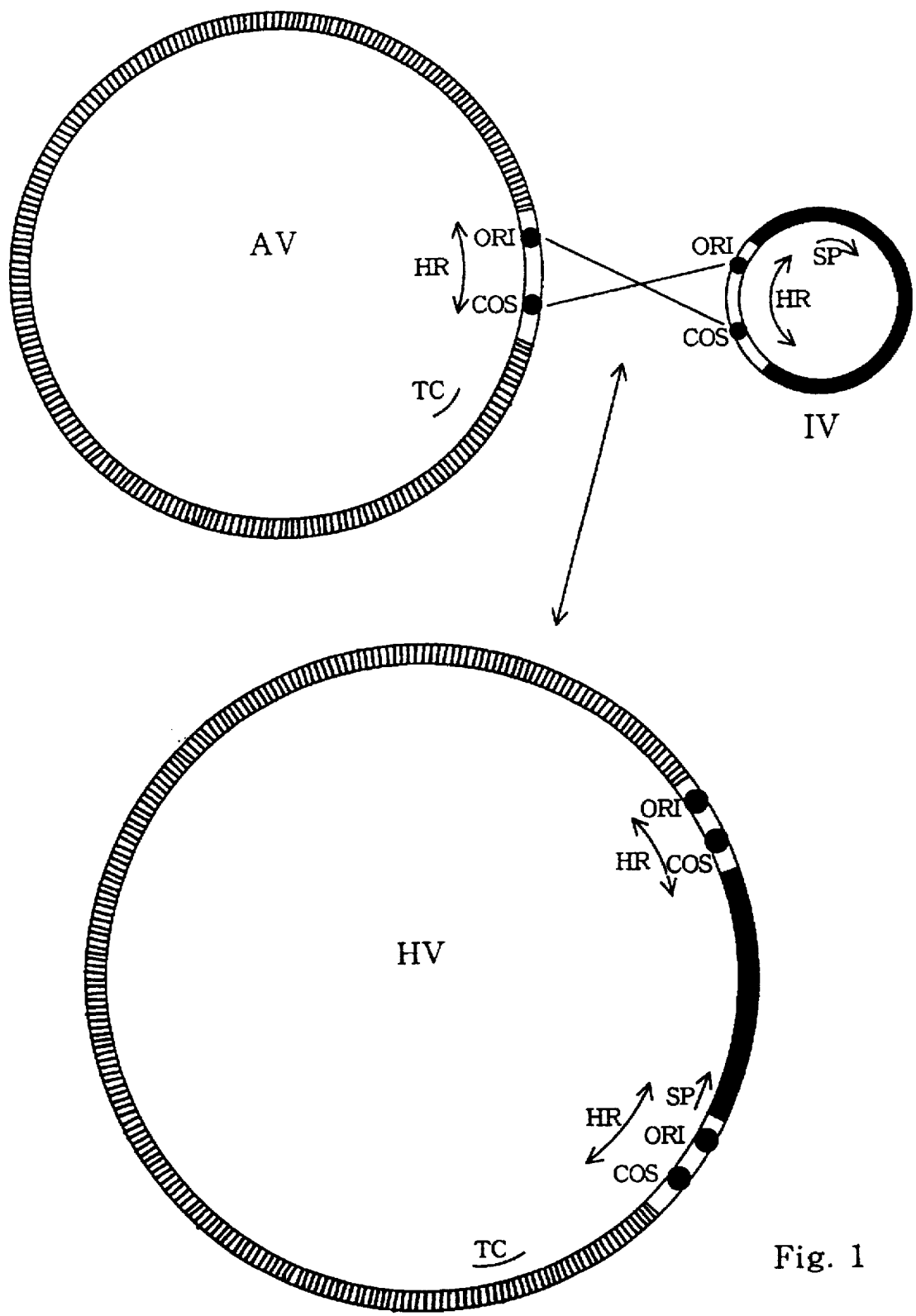
FIG. 1 schematically shows the phenomenon that a hybrid vector is prepared from an acceptor vector and an intermediate vector by homologous recombination in cells of a bacterium belonging to the genus Agrobacterium.
Figure 2:
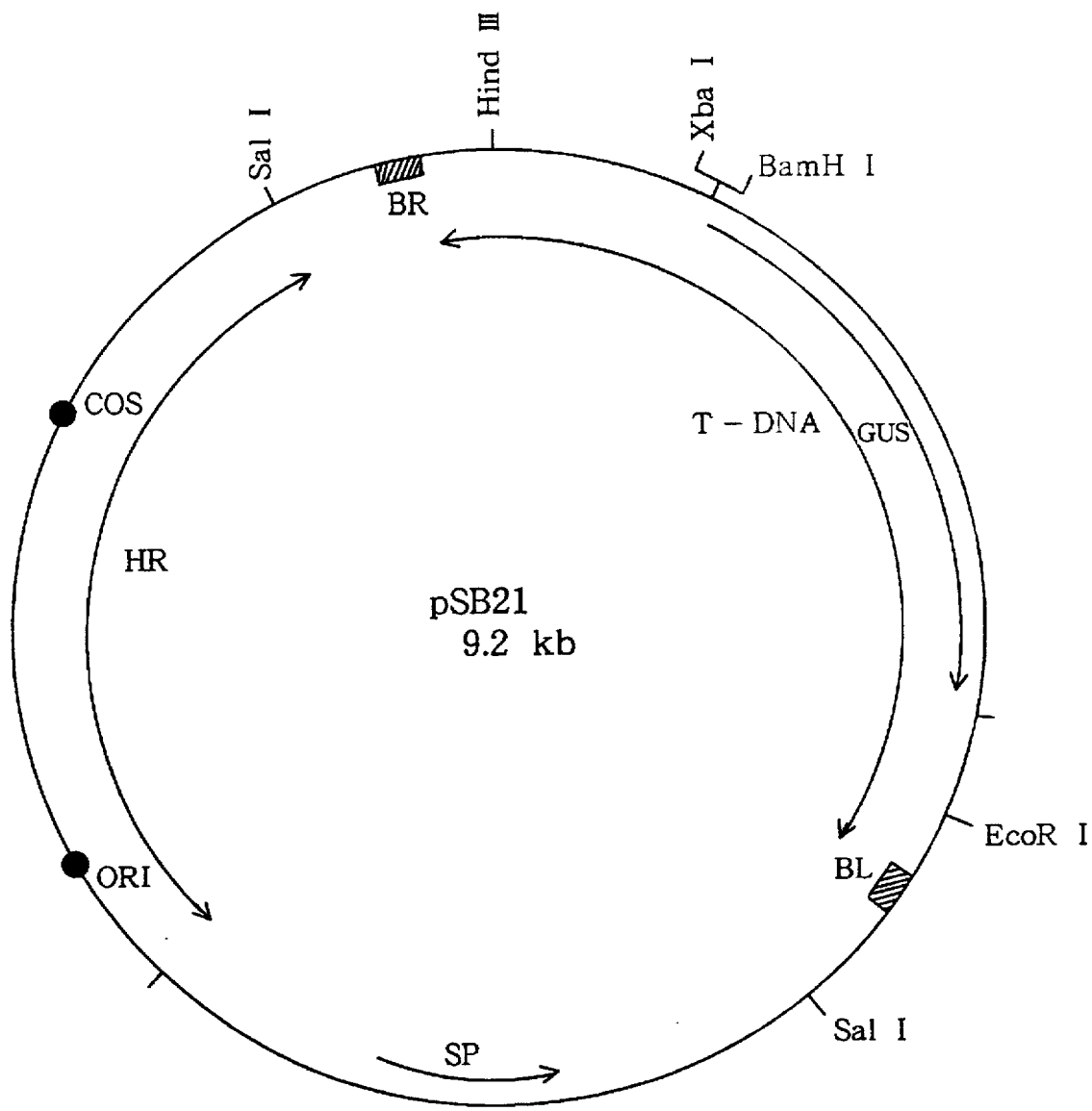
FIG. 2 shows constitution of pSB21.
Figure 3:
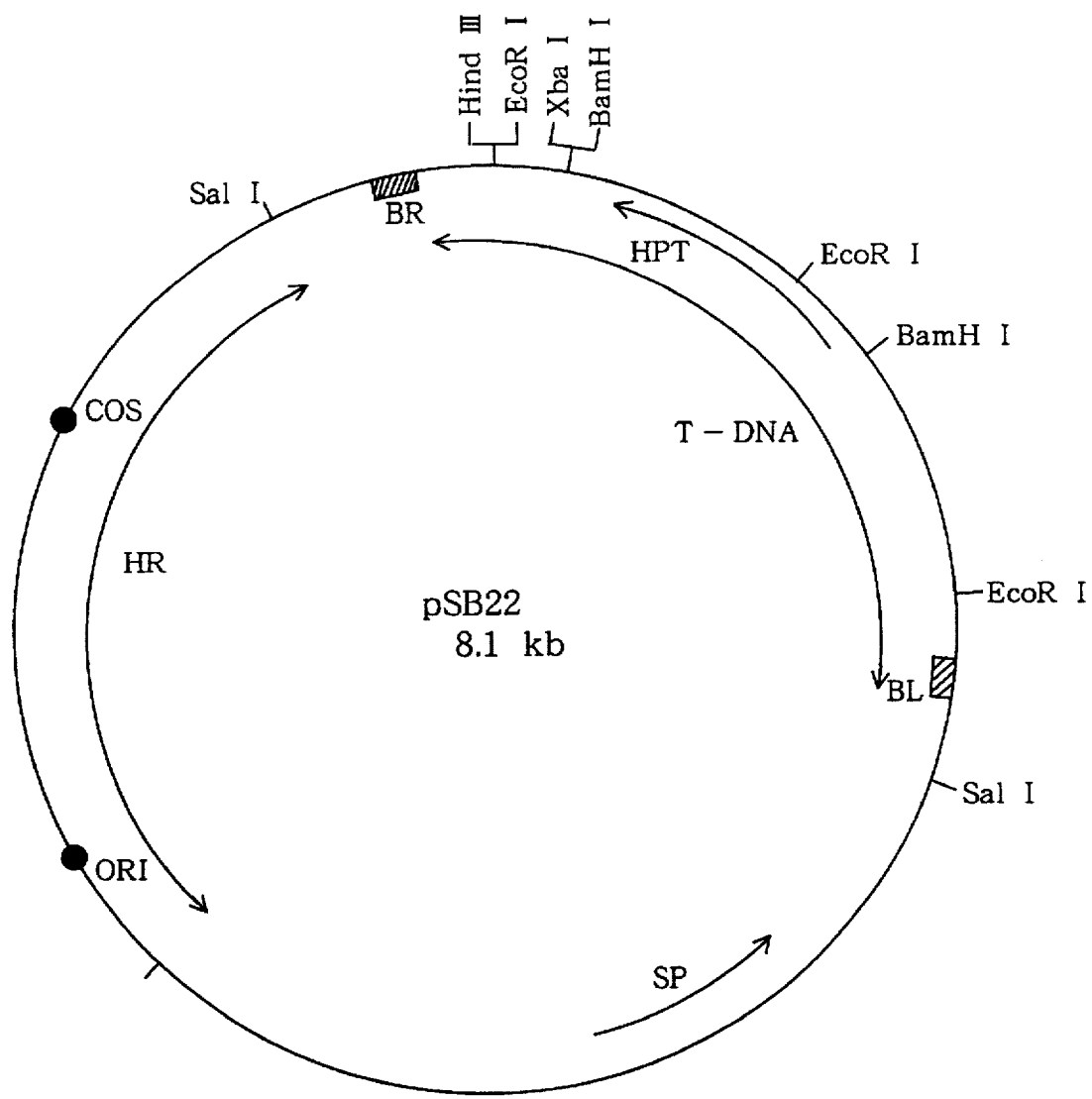
FIG. 3 shows constitution of pSB22.
Figure 4:
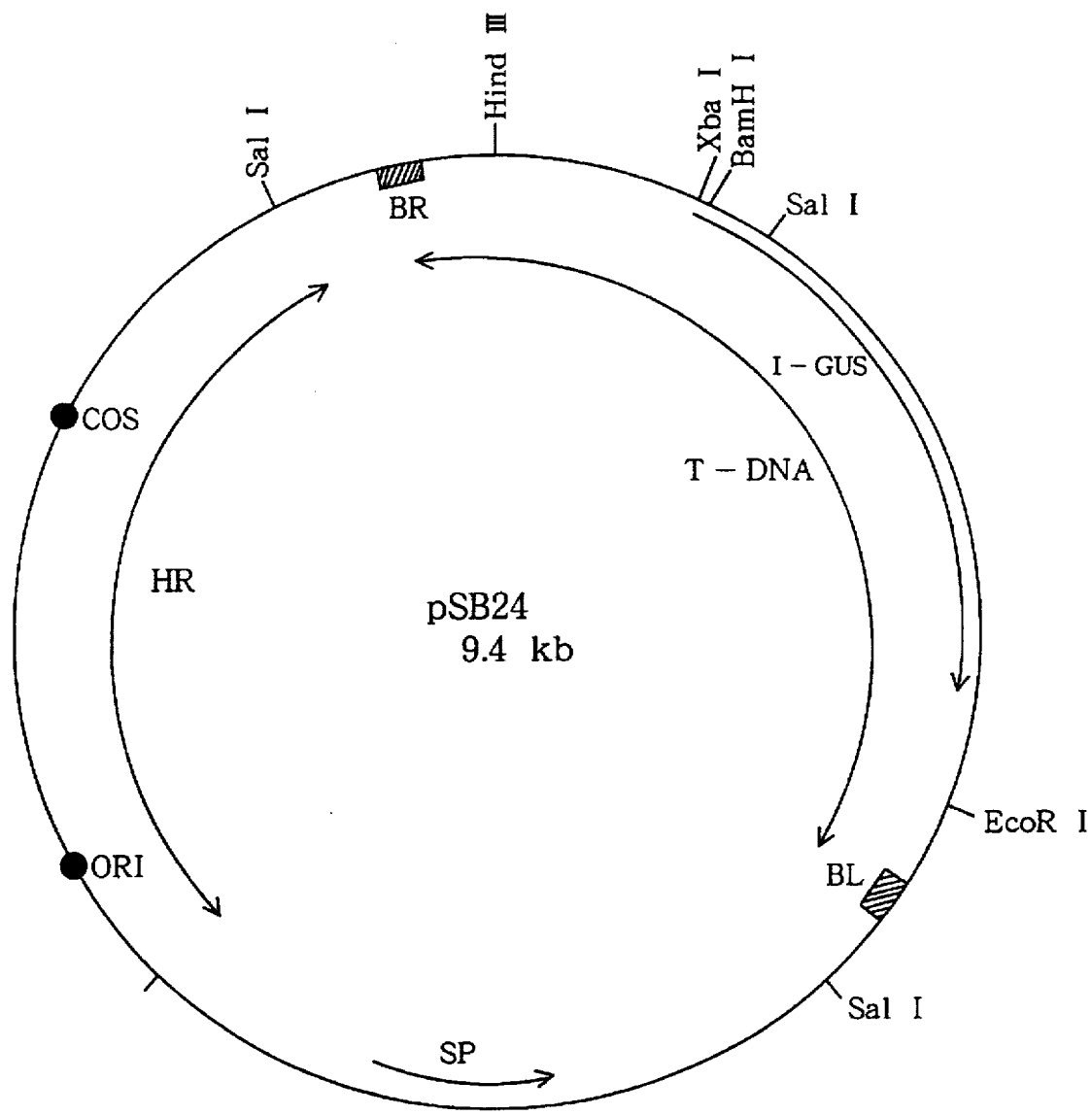
FIG. 4 shows constitution of pSB24.
Figure 5:
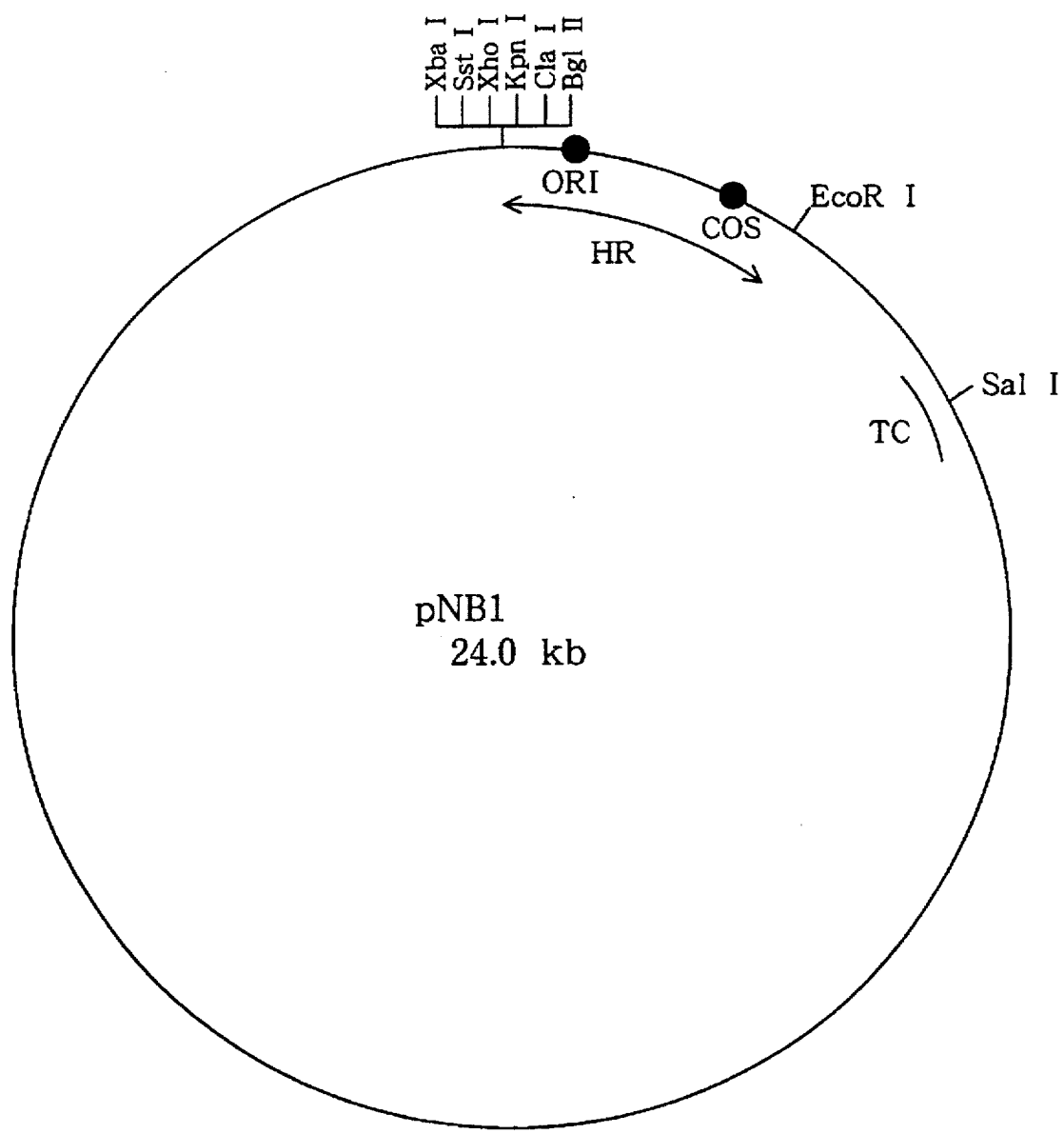
FIG. 5 shows constitution of pNB1.
Figure 6:
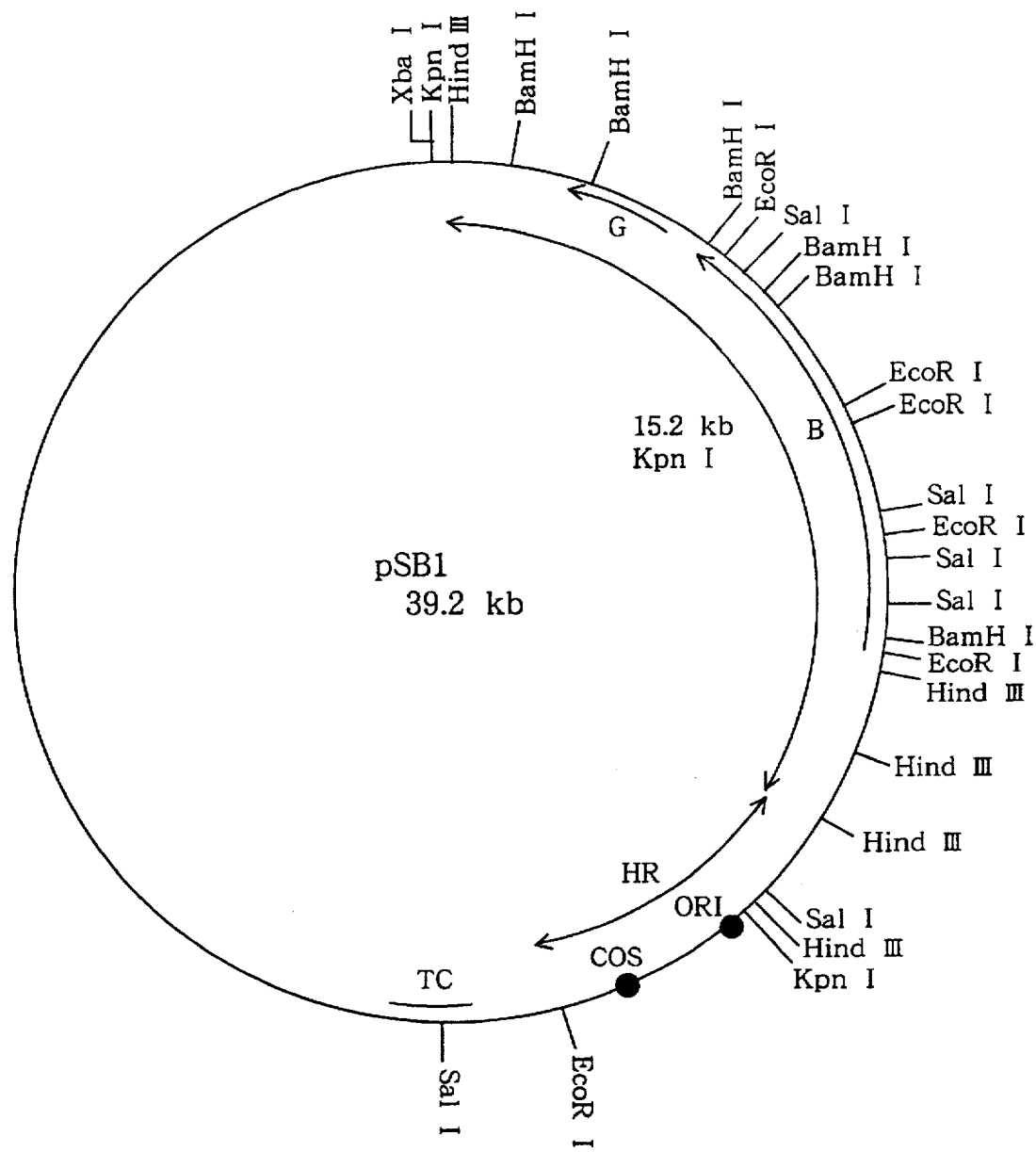
FIG. 6 shows constitution of pSB1.
Figure 7:
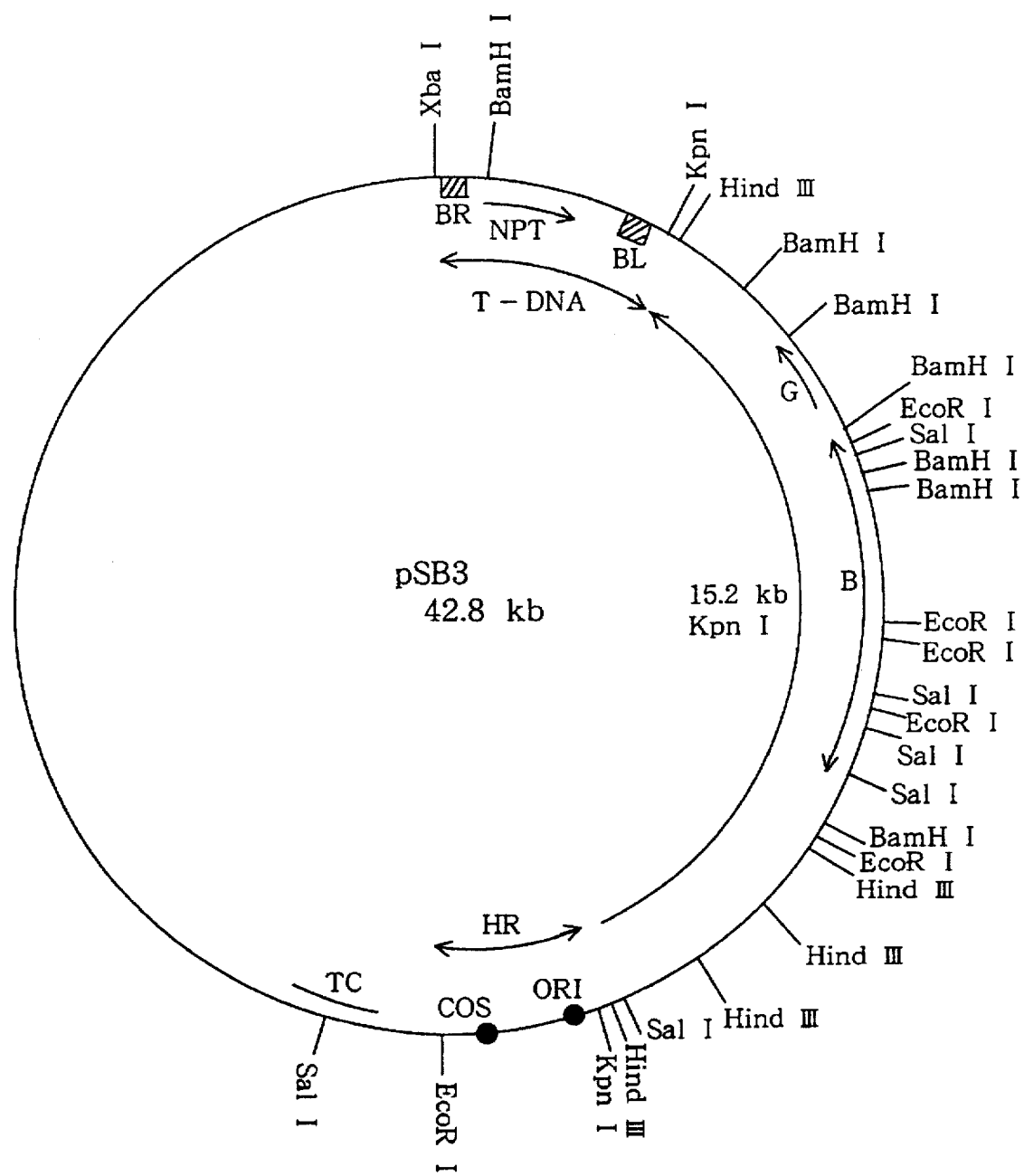
FIG. 7 shows constitution of pSB3.
Figure 8:
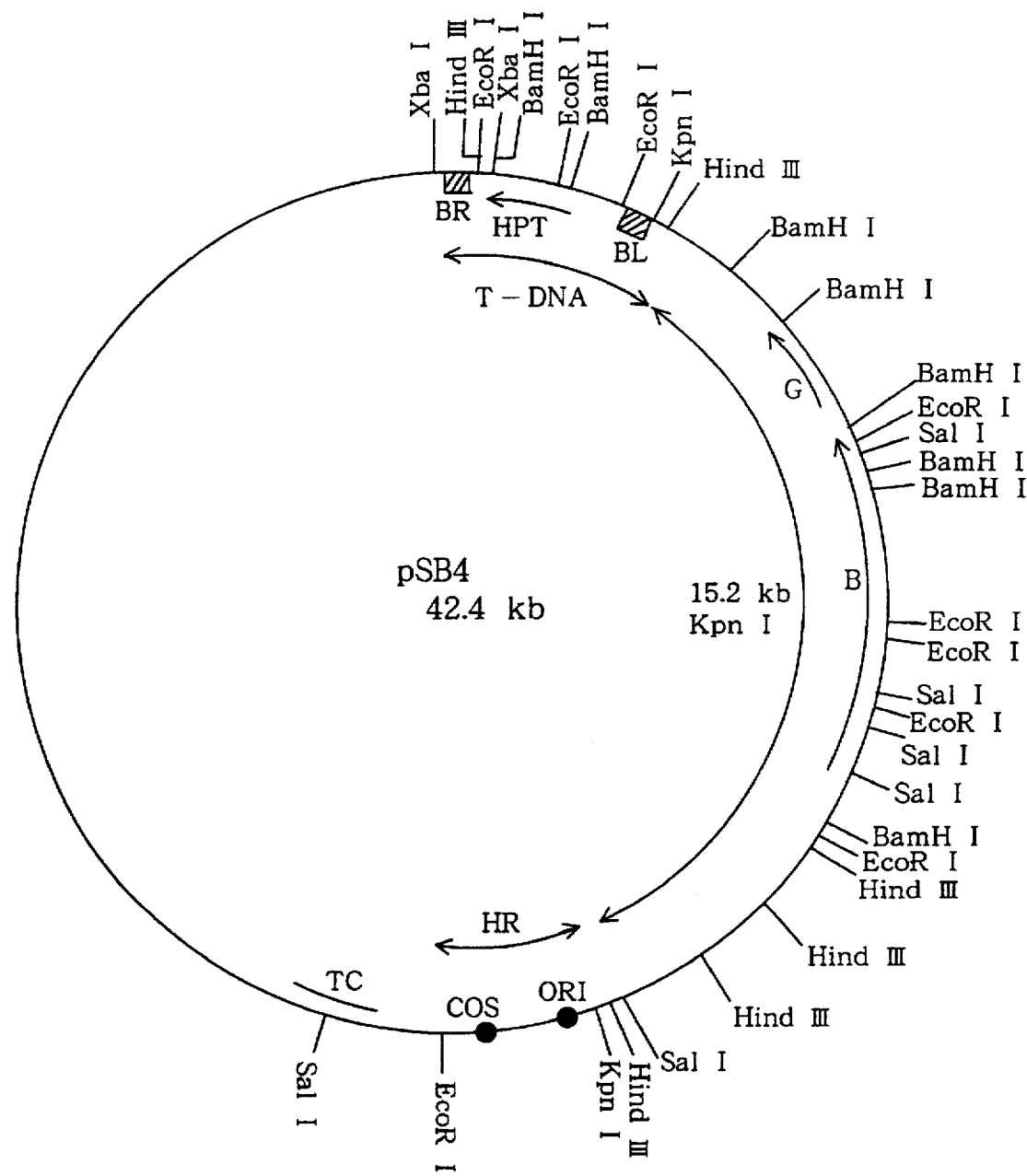
FIG. 8 shows constitution of pSB4.
Figure 9:
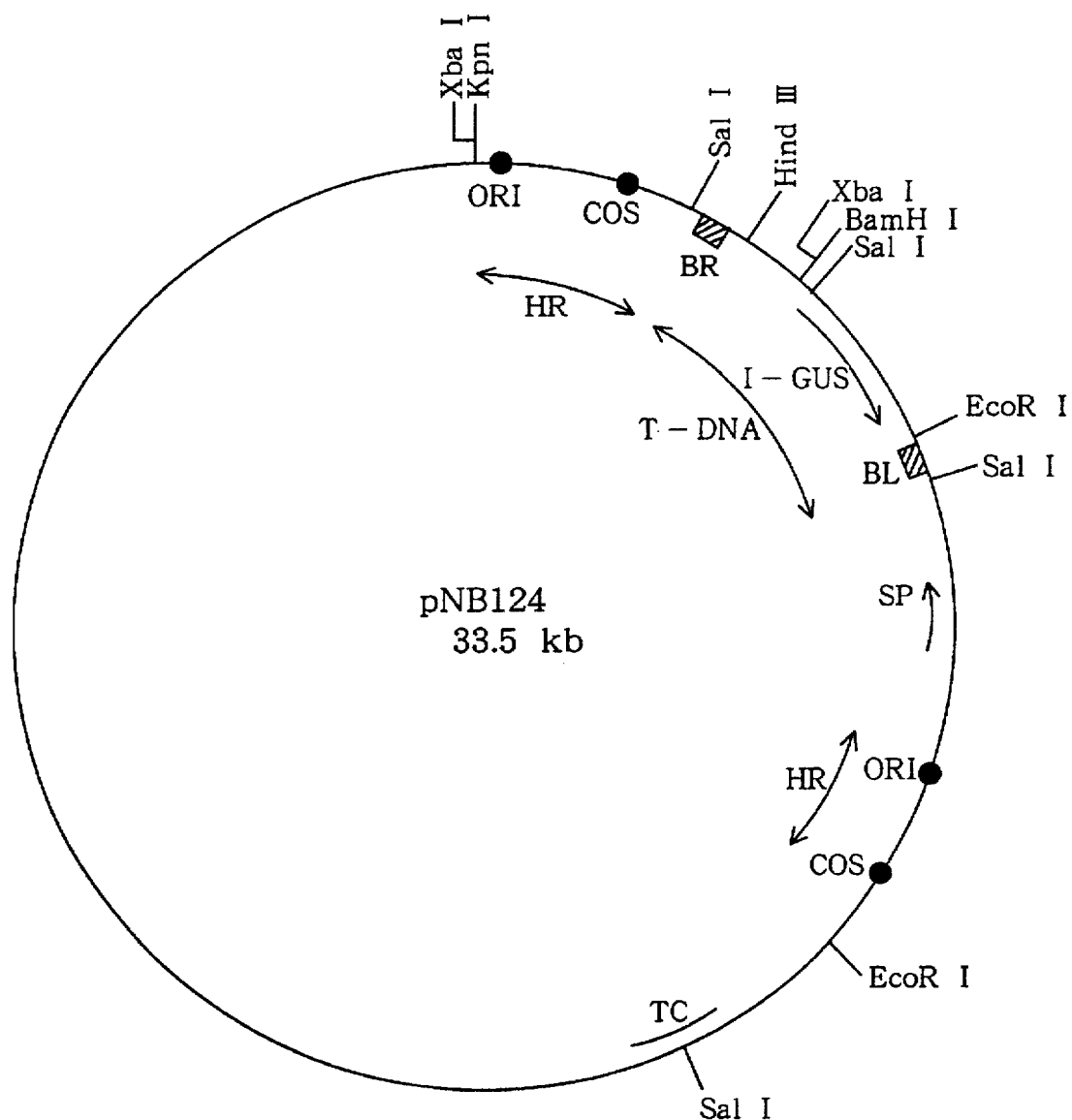
FIG. 9 shows constitution of pNB124 prepared by homologous recombination of pNB1 and pSB24.
Figure 10:
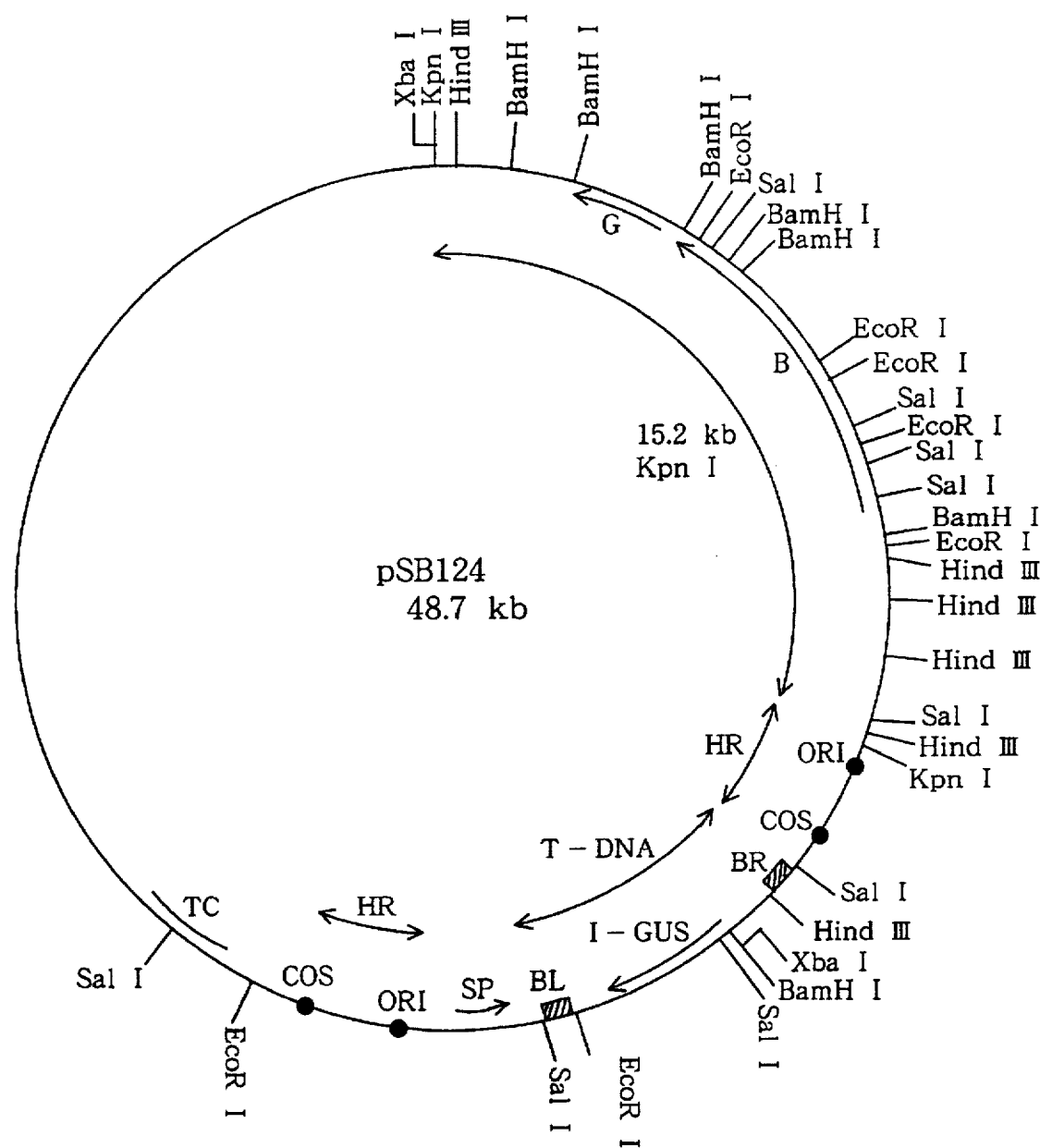
FIG. 10 shows constitution of pSB124 prepared by homologous recombination of pSB1 and pSB24.
Figure 11:
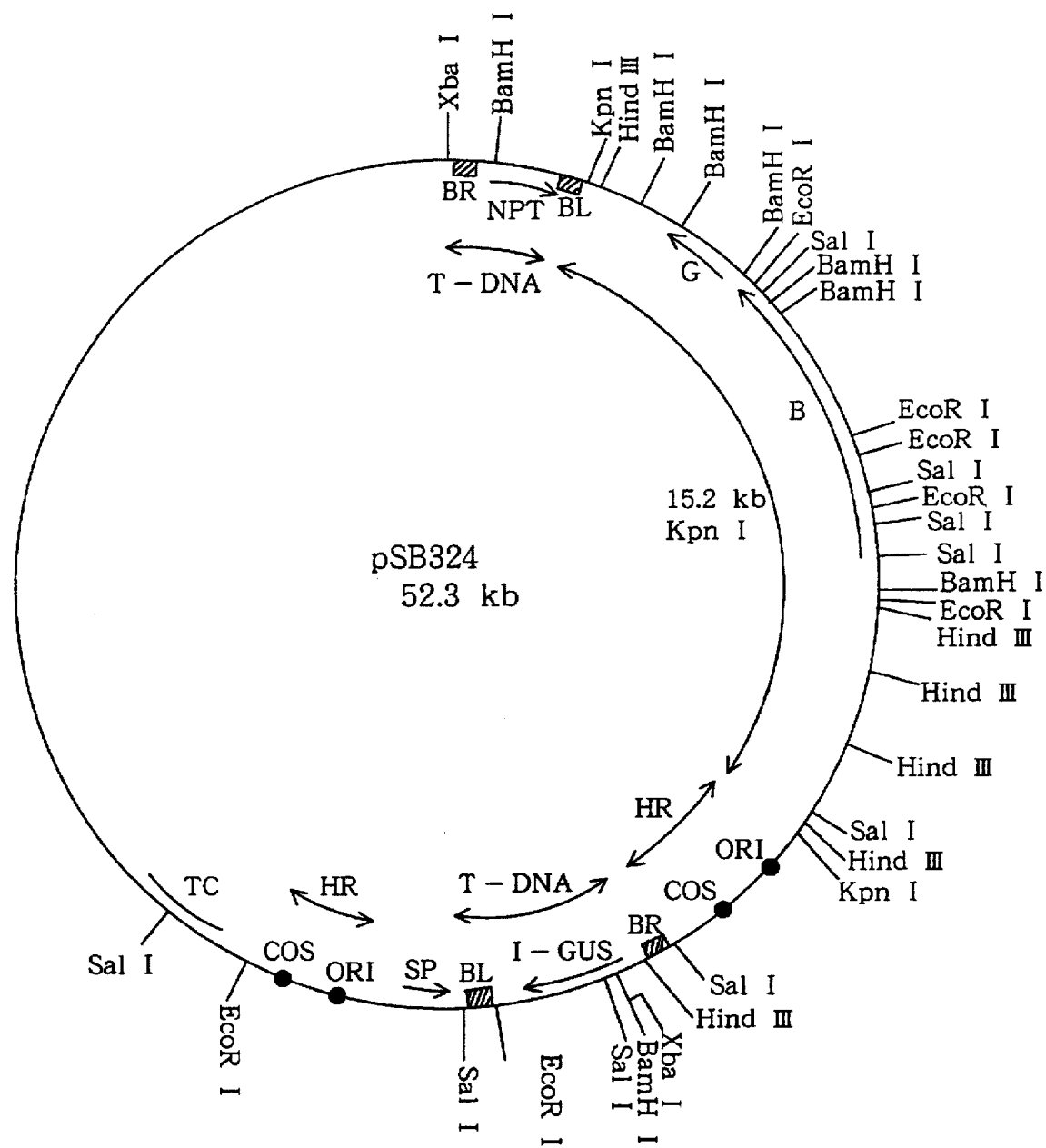
FIG. 11 shows constitution of pSB324 prepared by homologous recombination of pSB3 and pSB24.
Figure 12:
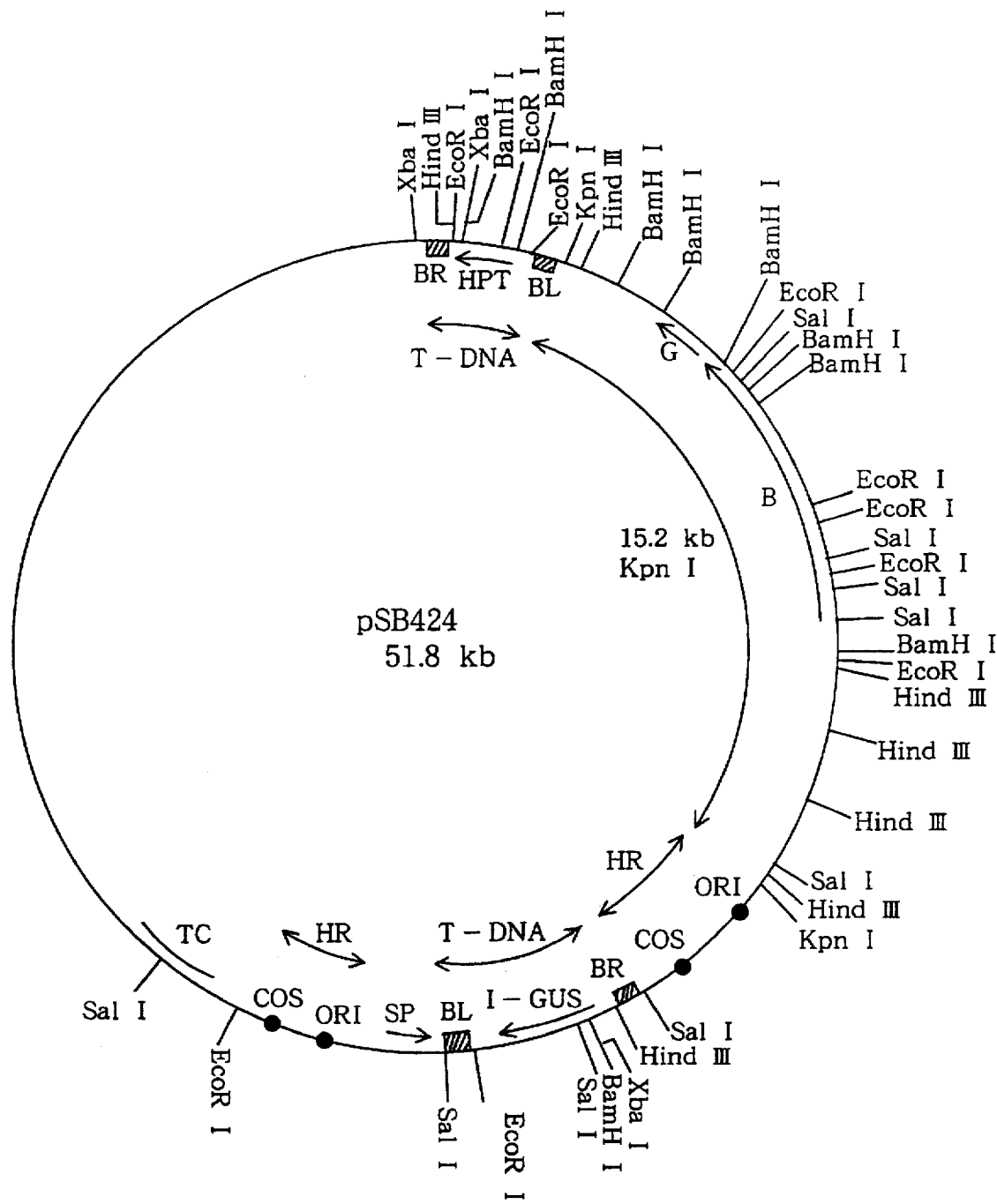
FIG. 12 shows constitution of pSB424 prepared by homologous recombination of pSB4 and pSB24.
Figure 13:
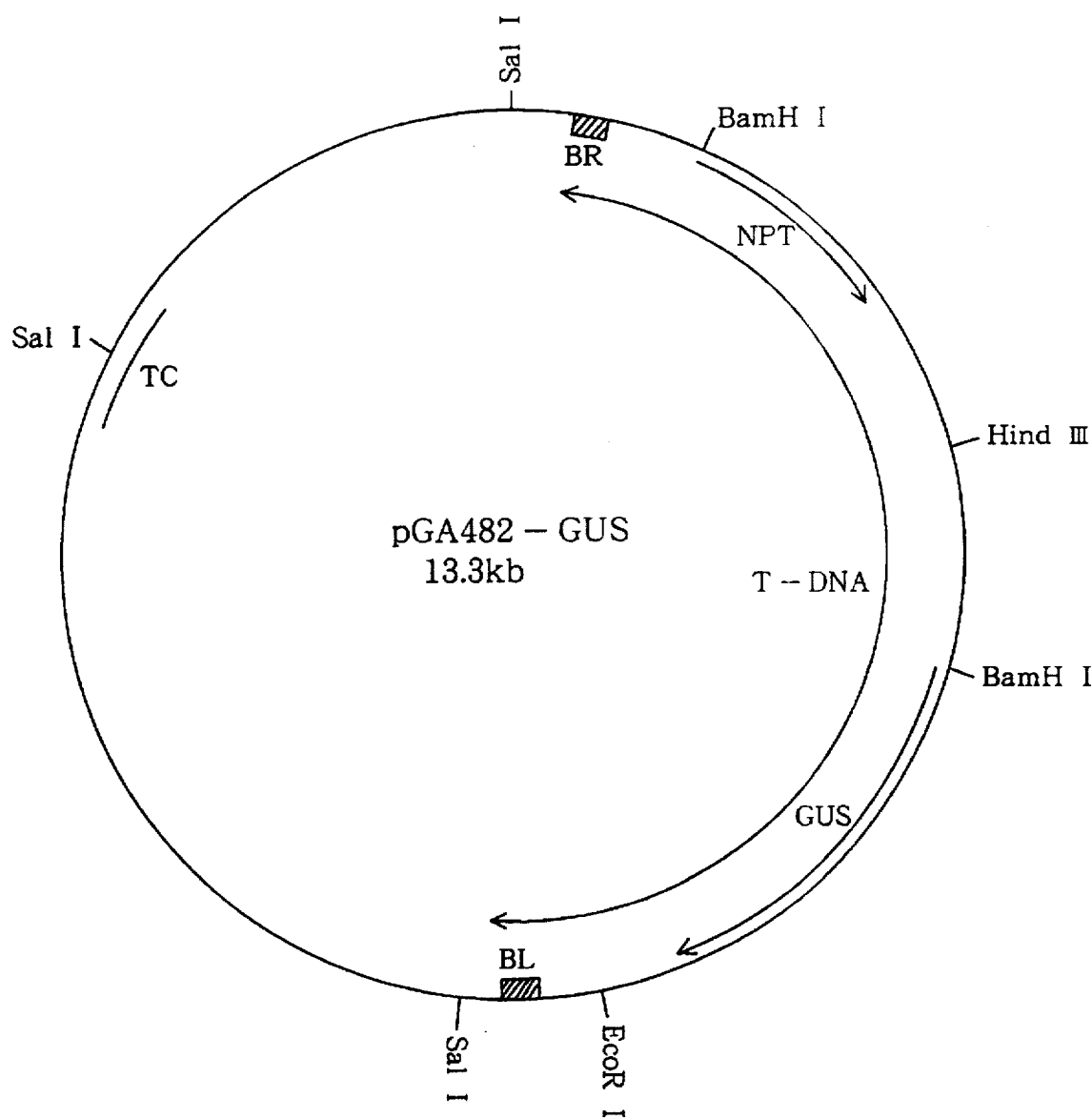
FIG. 13 shows constitution of pGA482-GUS.
Figure 14:
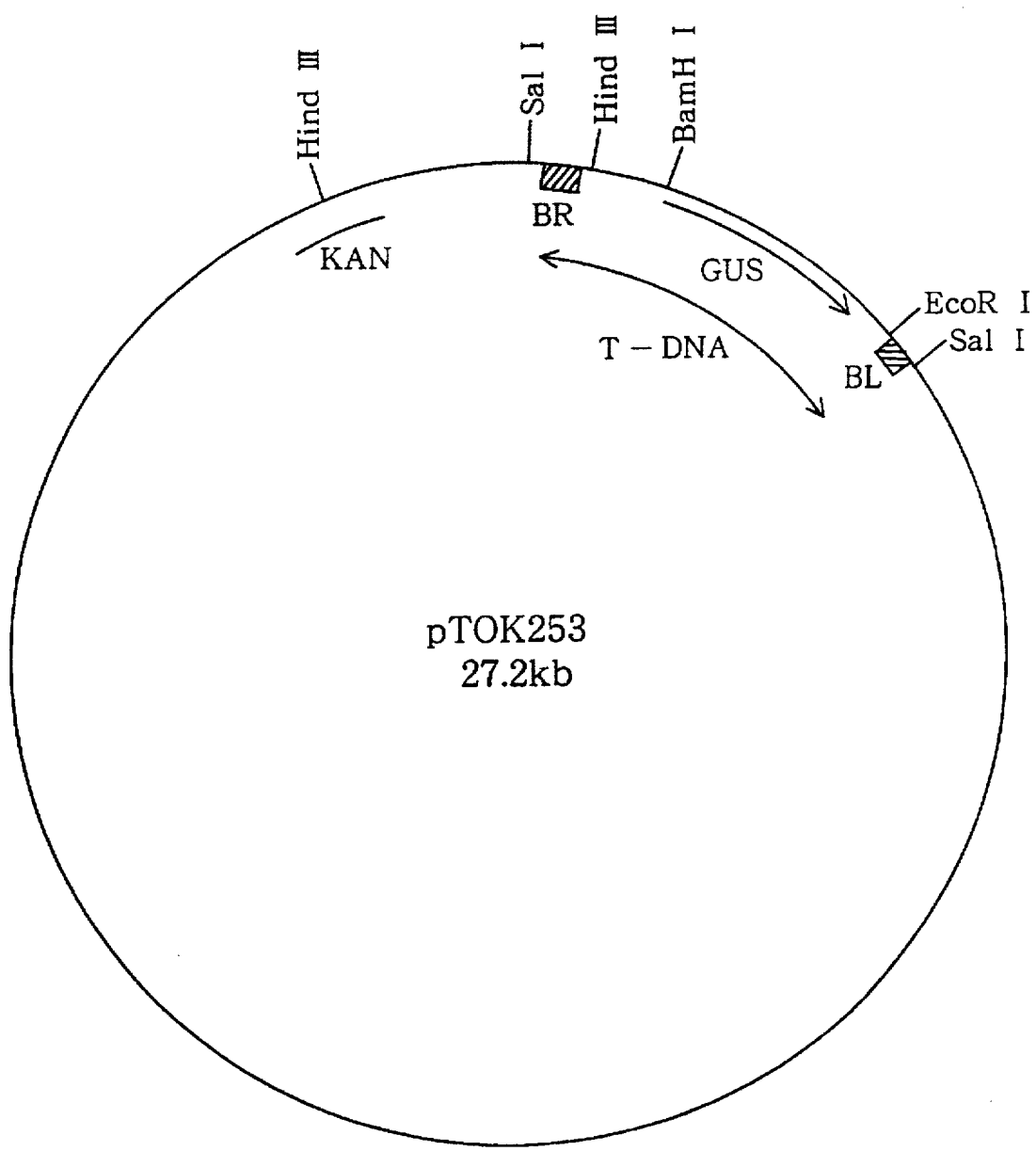
FIG. 14 shows constitution of pTOK253.

Reference symbols shown in the above-mentioned drawings represent the following meanings:

AV: acceptor vector;

IV: intermediate vector;

HV: hybrid vector;

HR: a fragment contained in both acceptor vector and hybrid vector, homologous recombination occurs between DNA sequences contained in this fragment;

ORI: replication origin of ColE1;

COS: cos site of λ phage;

SP: spectinomycin resistance gene which functions in *Escherichia coli* and a bacterium belonging to the genus Agrobacterium;

TC: tetracycline resistance gene which functions in *Escherichia coli* and a bacterium belonging to the genus Agrobacterium;

KAN: kanamycin resistance gene which functions in *Escherichia coli* and a bacterium belonging to the genus Agrobacterium;

NPT: kanamycin resistance gene to which NOS promoter that functions in plant cells is ligated. This gene gives also to *Escherichia coli* and a bacterium belonging to the genus Agrobacterium a low degree of resistance.

HPT: hygromycin resistance gene to which 35S promoter that functions in plant cells is ligated. This gene gives also to a bacterium belonging to the genus Agrobacterium a low degree of resistance.

GUS: GUS gene to which 35S promoter that functions in plant cells is ligated;

I-GUS: GUS gene containing intron, to which 35S promoter that functions in plant cells is ligated;

T-DNA: a DNA fragment transferred from a bacterium belonging to the genus Agrobacterium to plants;

BR: right border sequence of T-DNA;

BL: left border sequence of T-DNA;

15.2 kb KpnI: KpnI fragment having a size of 15.2 kb originated from the virulence region of pTiBo542;

B: virB gene of pTiBo542;

G: virG gene of pTiBo542.

BEST MODE FOR CARRYING OUT THE INVENTION

The plant which can be transformed by the method of the present invention may be any plant which is infected with a bacterium belonging to the genus Agrobacterium and is transformed thereby. Examples of such a plant include higher plants such as tobacco, rice, tomato, potato, petunia, maize, rape and the like, although the examples are not restricted thereto.

The method for transforming higher plants through a bacterium belonging to the genus Agrobacterium per se is well-known in the art. Examples of the bacterium belonging to the genus Agrobacterium, which may be employed for the transformation include *Agrobacterium tumefaciens*, *Agrobacterium rhizogenes* and the like. These Agrobacterium bacteria are soil bacteria which have abilities to transform plant cells and make tumors. These bacteria contain a tumor-inducing plasmid (Ti plasmid). Important regions in the Ti plasmid are the virulence region which participates in transformation and the T-DNA region in which the tumor-inducing genes transferred to plant cells are contained. In the T-DNA region, the regions indispensable to the transfer of the tumor-inducing genes are the regions at both ends thereof, which are called border sequences. Thus, in conventional methods for transformation of plants through an Agrobacterium bacterium, the plant is infected with an Agrobacterium bacterium which contains a plasmid containing a T-DNA in which the desired gene is inserted. In the method of the present invention too, the drug resistance gene and the desired gene to be introduced into plants are respectively inserted in T-DNAs.

In the method of the present invention, a plant is co-transformed with a first T-DNA containing a drug resistance gene used as a selection marker and a second T-DNA into which the DNA fragment which is desired to be introduced into the plant is inserted. As the drug resistance gene contained in the first T-DNA, kanamycin resistance gene and hygromycin resistance gene are preferred, although the drug resistance gene is not restricted thereto. Among the first and the second T-DNAs, at least the second T-DNA exists in the hybrid vector described below.

The hybrid vector is prepared by homologous recombination of an acceptor vector and an intermediate vector, which homologous recombination occurs in a bacterium belonging to genus Agrobacterium. The acceptor vector is a plasmid which can replicate in both Agrobacterium bacterium and *Escherichia coli*. The acceptor vector contains a DNA fragment which is homologous to a DNA fragment in the intermediate vector. Utilizing this DNA fragment, the acceptor vector can incorporate the intermediate vector therein by homologous recombination in an Agrobacterium bacterium. The intermediate vector is a plasmid which can replicate in *Escherichia coli* but can not replicate by itself in an Agrobacterium bacterium. The intermediate vector contains a DNA fragment which is homologous to the DNA fragment contained in the acceptor vector. The intermediate vector can be incorporated into the acceptor vector by homologous recombination through the DNA fragment. Once incorporated into the acceptor vector, the intermediate vector can be maintained in the bacterium belonging to the genus Agrobacterium.

The above-mentioned acceptor vector contains (a) a DNA region having a function to replicate a plasmid in the bacterium belonging to the genus Agrobacterium and *Escherichia coli*, (b) a DNA region containing virB gene and virG gene in virulence region of Ti plasmid pTiBo542 of *Agrobacterium tumefaciens*, and (c) a DNA region which is homologous with a part of the intermediate vector, which is subjected to homologous recombination in the bacterium belonging to the genus Agrobacterium.

The Ti plasmid pTiBo542 is a Ti plasmid contained in *Agrobacterium tumefaciens* A281 (ATCC 37349), which is known for its high ability of the virulence region (Hood et al., Bio/Technol. 2:702–709, 1984; Hood et al., J. Bacteriol., 168:1283–1290, 1986; Komari et al., J. Bacteriol., 166:88–94, 1986; Jin et al., J. Bacteriol. 169:4417–4425, 1987; and Komari, Plant Science, 60:223–229, 1989). The virB and virG genes in the virulence region of pTiBo542 are known and described in these references. Since the virB and virG genes in the virulence region of pTiBo542 are contained in the DNA fragment having a size of 15.2 kb, which is obtained by treating pTiBo542 with a restriction enzyme KpnI, this fragment may be used in the present invention too. The acceptor vectors per se containing the above-mentioned regions (a), (b) and (c) are known and described, for example, in Japanese Laid-open Patent Application (Kokai) No. 4-222527 and EP-A-0 504 869.

On the other hand, the intermediate vector contains (i) a DNA region having a function to replicate a plasmid in *Escherichia coli*, which does not function in the bacterium belonging to the genus Agrobacterium, (ii) a DNA region which is homologous with a part of the acceptor vector, which is subjected to homologous recombination in the bacterium belonging to the genus Agrobacterium, and (iii) a DNA region which constitutes at least a part of the second T-DNA.

Although a part of the above-mentioned second T-DNA may be contained in the above-mentioned acceptor vector, it is preferred that the whole second T-DNA be contained in the intermediate vector because the efficiency of introducing the desired DNA fragment into the plant is high. The desired DNA fragment which is to be introduced into the plant may preferably be inserted into the second T-DNA in the intermediate vector utilizing a restriction site. Intermediate vectors per se containing the above-mentioned regions (i), (ii) and (iii) are known and are described, for example, in Japanese Laid-open Patent Application (Kokai) No. 4-222527 and EP-A-0 504 869.

The homologous recombination between the above-described acceptor vector and the above-described intermediate vector may be carried out by a known method Herrera-Esterella L. et al., EMBO J. 2:987-995, 1983; Horsch R. H. et al., Science 223:496-498, 1984).

The above-described first T-DNA may exist either in the hybrid vector containing the above-described second T-DNA or in another plasmid. In the latter case, the hybrid vector and the other vector may be contained in the same cell of Agrobacterium bacterium or in separate cells of Agrobacterium bacteria (two-strain method). However, since the probability that the selected drug resistant cell also contains the second T-DNA is significantly higher in the case where the first and second T-DNAs exist in a single hybrid vector, it is preferred that the first T-DNA also exists in the hybrid vector. Further, surprisingly, even if the first and the second T-DNAs are located in a single vector, these are independently introduced into plants and can be genetically segregated in the next generation. The method for efficiently co-transforming the plants with T-DNAs located in a single vector was first developed by the present inventors and the fact that they may be genetically independently introduced into plant at a high frequency was first discovered by the present inventors.

In cases where the first T-DNA exists in the hybrid vector, to increase the probability that the first and second T-DNAs are genetically independently introduced into plants, it is preferred that the distance between the first T-DNA and the second T-DNA is large. For this purpose, the first T-DNA is preferably originated from the acceptor vector. Further, for this purpose, it is preferred that the first T-DNA and the second T-DNA be separated in the hybrid vector by (1) the DNA region having a function to replicate a plasmid in the bacterium belonging to the genus Agrobacterium and *Escherichia coli*, and (2) the DNA region containing virB gene and virG gene in virulence region of Ti plasmid pTiBo542 of *Agrobacterium tumefaciens*.

The hybrid vector can be introduced into the bacterium belonging to the genus Agrobacterium by known methods such as triple cross method of bacteria (Ditta G. et al., Proc. Natl. Acad. Sci. U.S.A., 77:7347-7351, 1980).

As the bacterium belonging to the genus Agrobacterium which is used for transformation of plants, those which are conventionally used for this purpose may be employed. That is, those having a plasmid originated from Ti plasmid or Ri plasmid, that does not contain T-DNA but contains the virulence region necessary for the transfer of T-DNA to plants, may preferably be employed. An example of such a bacterium is *Agrobacterium tumefaciens* LBA4404 (Hoekema et al., Nature, 303:179-180, 1983), although not restricted thereto. Such an Agrobacterium bacterium to which the above-mentioned hybrid vector or a plasmid containing the first T-DNA (in case of double line method) is used for the transformation.

Then the plant is transformed using the Agrobacterium bacterium to which the hybrid vector or a plasmid containing the first T-DNA (in case of two-strain method) is introduced. This may be attained by culturing plant cells such as fragments of cotyledon of the plant in a liquid medium containing the Agrobacterium bacterium. in the case of two-strain method, the plant cells are cultured in a liquid medium containing the two types of Agrobacterium cells. The transformation method per se is known and described, for example, in Japanese Laid-open Patent Application (Kokai) No. 4-222527 and EP-A-0 504 869.

Among the plant cells subjected to the transformation treatment, cells which acquired drug resistance by virtue of the drug resistance gene contained in the first T-DNA are selected. Whole plants are then regenerated from these cells according to a conventional method.

The thus obtained plants may also contain the second T-DNA with a considerable probability. In the Examples below, in cases where the first and the second T-DNAs are located in the same hybrid vector, not less than about 50% of the obtained plants also contained the second T-DNA, and even in the case of double line method, about 35% of the obtained plants also contained the second T-DNA.

It was confirmed in most of the transformed plants containing the first and the second T-DNAs that the first T-DNA and the second T-DNA are independently inherited. More particularly, in the Examples below, the percentage of the transformed plants in which it was confirmed that the first T-DNA and the second T-DNA are independently inherited is 79% in cases where the first and the second T-DNAs exist in the single hybrid vector, or 71% in the case of two-strain method. Therefore, by cultivating these transformed plants, plants which contain the second T-DNA but do not contain the first T-DNA can be obtained in the next generation.

The present invention also provides a hybrid vector comprising a first T-DNA containing (1) a gene giving a drug resistance, which functions in a plant, and (2) a second T-DNA having a restriction site;

the hybrid vector being prepared by homologous recombination between an acceptor vector and an intermediate vector in a bacterium belonging to the genus Agrobacterium;

the acceptor vector containing at least
(a) a DNA region having a function to replicate plasmid in the bacterium belonging to the genus Agrobacterium and *Escherichia coli*,
(b) a DNA region containing virB gene and virG gene in virulence region of Ti plasmid pTiBo542 of *Agrobacterium tumefacien*, and
(c) a DNA region which is homologous with a part of the intermediate vector, which is subjected to homologous recombination in the bacterium belonging to the genus Agrobacterium;

the intermediate vector containing at least
(i) a DNA region having a function to replicate a plasmid in *Escherichia coli*, which does not function in the bacterium belonging to the genus Agrobacterium,
(ii) a DNA region which is homologous with a part of the acceptor vector, that is subjected to homologous recombination in the bacterium belonging to the genus Agrobacterium, and
(iii) a DNA region which constitutes at least a part of the second T-DNA.

This hybrid vector is the same as the hybrid vector employed in the above-described method according to the present invention except that the desired DNA fragment has not been inserted into the second T-DNA. After inserting the desired DNA fragment into the second T-DNA utilizing the restriction site therein, the resulting hybrid vector can be used as the hybrid vector described above.

EXAMPLES

The present invention will now be described more concretely by way of examples. However, the examples are presented for the illustration purpose only and should not be interpreted in any restrictive way.

Example 1
Construction of Plasmid

Unless otherwise specified, the operations for constructing the plasmid were carried out in accordance with Sambrook et al., Molecular Cloning, A Laboratory Manual, Second Edition, Cold Spring harbor Laboratory Press, Cold Spring Harbor, N.Y., 1989.

Construction of Intermediate Vectors pSB21 and pSB24 pBR322 was digested with EcoRI and ClaI and treated with T4 DNA polymerase. A ClaI linker (5'-CATCGATG-3') was inserted into the resultant and circularized. The DraI-EcoRI fragment having a size of 2.6 kb containing a spectinomycin resistant gene (SP gene) of transposon Tn7 (DeGreve et al., Plasmid 6:235–248, 1981) was cloned into the above-mentioned plasmid at the site between EcoRV and EcoRI. After cutting the plasmid with EcoRI, the plasmid was re-circularized after the treatment with T4 DNA polymerase to remove the EcoRI site. The 2.4 kb ClaI fragment containing the SP gene of this plasmid was treated with T4 DNA polymerase and inserted into the SmaI site of pUC19 to obtain TOK107. The 2.7 kb EcoRI-HindIII fragment of pGA482 (An, Plant Physiol. 81:86–91, 1986) and the pTOK107 digested with EcoRI and HindIII were ligated to prepare pTOK170.

pTOK170 was digested with BamHI and BglII and circularized to obtain pYS138. pYS138 was digested with EcoRI and Asp718I and the resultant was treated with T4 DNA polymerase. To the resultant, a SalI linker (5'-GGTCGACC-3') was inserted and the plasmid was circularized to obtain pYS151. pYS151 was digested with SalI and a 4.7 kb SalI fragment containing T-DNA of pGA643 (An et al., Plant Molecular Biology Manual A3:1–19, Kluwer Academic, Dordrecht, 1988) was inserted into the resulting SalI site to obtain pTOK235.

pTOK235 was digested with SacII and the resultant was blunted by T4 DNA polymerase. A BglII linker (5'-CAGATCTG-3') or a HindIII linker (5'-CAAGCTTG-3') was inserted to the resulting plasmid and the resultant was circularized. The obtained plasmids were named pTOK245 and pTOK246, respectively.

pTOK246 was digested with HindIII and EcoRI to remove most part of the DNA in the T-DNA, and the 2.9 kb HindIII-EcoRI fragment of pBI221 (Jefferson, Plant Molecular Biology Reporter 5:387–405, 1987) was inserted therein to obtain pSB21. In the 2.9 kb HindIII-EcoRI fragment of pBI221, β-glucuronidase gene (GUS) which is expressed in plant cells is contained. pSB21 is an intermediate vector constituted by (i) spectinomycin resistant gene which functions in Escherichia coli and in Agrobacterium; (ii) a fragment originated from 2.7 kb EcoRI-HindIII fragment of pGA482, which has a function to replicate the plasmid in Escherichia coli but not in Agrobacterium; and (iii) a fragment containing T-DNA region constituted by left and right border sequences and GUS gene therebetween.

Similarly, pTOK246 was digested with HindIII and EcoRI and 3.1 kb HindIII-EcoRI fragment of pIG221 (Ohta et al., Plant Cell Physiol. 31:805–813, 1990) was inserted therein to to obtain pSB24. In the fragment, a GUS gene in which an intron sequence is inserted (intron GUS) is contained. Intron GUS is efficiently expressed in plant cells, but not expressed in Escherichia coli and Agrobacterium at all by virtue of the intron. pSB24 is an intermediate vector which is the same as pSB21 except that the intron GUS gene is contained in place of GUS gene.

Construction of pSB22 pGL2 constituted by a hygromycin resistant gene (HPT, Gritz et al., Gene 25:179–188, 1983) and pDH51 (Pietrazak et al., Nucleic Acids Res 14:5857–5868, 1986), which contains HPT gene that functions in plant cells, was digested with SalI. The digest was treated with T4 DNA polymerase and then circularized, thereby deleting a SalI site to obtain pTOK234. The obtained pTOK234 was digested with KpnI and then processed in the same manner as mentioned above, thereby deleting two KpnI sites to obtain pTOK244.

pTOK244 was digested with HindIII and then incompletely digested with EcoRI to isolate a fragment with a size of 1.9 kb. This fragment was inserted between HindIII site and EcoRI site of pTOK246 to obtain pSB22. pSB22 is an intermediate vector which is the same as pSB21 except that the GUS gene is exchanged with HPT gene.

Construction of pYS169 pGA482 was digested with HindIII and EcoRI and then treated with T4 DNA polymerase, followed by circularization, thereby deleting 2.7 kb HindIII-EcoRI fragment to obtain pYS169. pYS169 contains a T-DNA constituted by left and right border sequences of T-DNA and a kanamycin resistant gene (NPT) located therebetween. The NPT gene has an ability to give resistance to kanamycin to Escherichia coli and Agrobacterium.

Construction of pNB1 pVCK101 (Knauf et al., Plasmid 8:45–54, 1982) was digested with EcoRI and then treated with T4 DNA polymerase, followed by circularization, thereby deleting an EcoRI site. By digesting the resultant with BglII and then circularization, a BglII site was deleted. This plasmid was named pVCK101Q. pVCK101Q was digested with HindIII and XhoI and ligated to pUC18 digested with HindIII and SalI to obtain pTOK150. pTOK150 was digested with HindIII and then treated with T4 DNA polymerase. An EcoRI linker (5'-CCGAATTCGG-3') was inserted and the resultant was closed, thereby converting the HindIII site to EcoRI site to obtain pTOK239.

pGA482 was digested with HpaI and a XhoI linker (5'-CCTCGAGG-3') was inserted to obtain pTOK236. pTOK236 was digested with XbaI and EcoRI to isolate a fragment having a size of 2.6 kb. pTOK239 was digested with EcoRI and XbaI to remove a fragment having a size of 2.7 kb, and 2.7 kb XbaI-EcoRI fragment of pTOK236 was inserted to obtain pNB1. pNB1 is a kind of acceptor vector but does not contain T-DNA or a DNA originated from the virulence region.

Construction of pNB3 and pNB4 pNB1 was digested with XhoI and a SalI fragment having a size of 3.5 kb which comprises T-DNA that contains the NPT gene of pYS169 was inserted to obtain pNB3. pNB3 is a kind of acceptor vector and comprises T-DNA which contains NPT gene.

pNB1 was digested with XhoI and 3.0 kb SalI fragment comprising T-DNA that contains the HPT gene of pSB22 was inserted to obtain pNB4. pNB4 is a kind of acceptor vector and comprises T-DNA containing HPT gene.

Construction of pSB1, pSB3 and pSB4 pNB1, pNB3 and pNB4 were digested with KpnI and the 15.2 kb KpnI fragment containing virB gene and virG gene of the virulence region of pTiBo542 (American Type Culture Collection, Accession No. 37349) was inserted to prepare three types of plasmids which were named pSB1, pSB3 and pSB4, respectively.

pSB1 is a kind of acceptor vector. In cases where a hybrid vector is prepared by incorporating therein an intermediate vector containing a T-DNA, a super binary vector may be constituted by combining the hybrid vector with a helper plasmid.

pSB3 is an acceptor vector comprising a T-DNA containing NPT gene as a selection marker gene. This vector has a site into which an intermediate vector can be inserted, the site being separated from the T-DNA by the 15.2 kb KpnI fragment containing virB gene and virG gene of the virulence region of pTiBo542. pSB3 may constitute a super binary vector by combining it or a hybrid vector prepared by incorporating an intermediate vector, with a helper plasmid. In cases where a hybrid vector is prepared by incorporating an intermediate vector containing a T-DNA, this hybrid vector is characterized by comprising two T-DNAs, that is, the first T-DNA containing NPT gene as a selection marker gene and a second T-DNA located at a site apart from the first T-DNA by not less than 15.2 kb.

pSB4 is an acceptor vector comprising a T-DNA containing HPT gene as a selection marker gene. This vector has a site into which an intermediate vector can be inserted, the site being separated from the T-DNA by the 15.2 kb KpnI fragment containing virB gene and virG gene of the virulence region of pTiBo542. pSB4 may constitute a super binary vector by combining it or a hybrid vector prepared by incorporating an intermediate vector, with a helper plasmid. In cases where a hybrid vector is prepared by incorporating an intermediate vector containing a T-DNA, this hybrid vector is characterized by comprising two T-DNAs, that is, the first T-DNA containing NPT gene as a selection marker gene and a second T-DNA located at a site apart from the first T-DNA by not less than 15.2 kb.

Construction of pTOK253 pVCK102 (Knauf et al., Plasmid 8:45–54, 1982) was digested with SalI and 4.1 kb SalI fragment containing the T-DNA of pSB21 was inserted to prepare pTOK253. pTOK253 is a plasmid which can constitute a binary vector by combination with a helper plasmid. The T-DNA in this plasmid contains GUS gene which functions in plant cells but does not contain a drug resistant gene.

Construction of pGA482-GUS pGA482 was digested with HindIII and EcoRI and 2.9 kb HindIII-EcoRI fragment of pBI221 was inserted to obtain pGA482-GUS. pGA482 is a plasmid which can constitute a binary vector by combination with a helper plasmid and the T-DNA thereof contains kanamycin resistant gene (NPT) which functions in plant cells. pGA482-GUS is a plasmid which can constitute a binary vector by combination with a helper plasmid and the T-DNA thereof contains GUS gene and kanamycin resistant gene (NPT), which function in plant cells.

Example 2

Preparation of bacteria belonging to genus Agrobacterium

In this example, bacteria belonging to genus Agrobacterium were cultured in AB medium (Chilton et al., Proc. Natl. Acad. Sci. U.S.A. 71:3672–3676, 1974) at 28° C. As required, media to which tetracycline (10 μg/ml), kanamycin (100 μg/ml), hygromycin (50 μg/ml) or spectinomycin (50 μg/ml) was added were used.

By the method of Ditta et al., (Proc. Nat. Acad. Sci. U.S.A. 77:7347–7351, 1980), pNB1, pSB1, pSB3 and pSB4 were introduced into *Agrobacterium tumefaciens* strain LBA4404 (Hoekema et al., Nature 303:179–180, 1983). LBA4404 is a strain which contains a disarmed Ti plasmid pAL4404 from which T-DNA was removed. pAL4404 retains a complete virulence region and frequently used as a helper plasmid of binary vectors. Bacteria belonging to genus Agrobacterium to which a plasmid was introduced will be hereinbelow indicated by the name of strain followed by name of plasmid in parentheses, such as, for example, LBA4404(pNB1).

To LBA4404(pNB1) which is a tetracycline resistant strain, pSB21 having a spectinomycin resistant gene was introduced by the method of Ditta et al. and bacterial cells which were resistant to both tetracycline and spectinomycin were selected, thereby obtaining LBA4404 containing a hybrid vector in which an intermediate vector pSB21 was introduced into pNB1. This hybrid vector was named pNB121.

In the similar manner, LBA4404 cells which respectively contain the hybrid vectors shown in Table 1 were prepared.

TABLE 1

| Construction of Hybrid Vector | | | | | | | |
|---|---|---|---|---|---|---|---|
| Name of Acceptor Vector | Drug Resistance of Acceptor Vector | Name of Intermediate Vector | Drug Resistance of Intermediate Vector | Name of Hybrid Vector | Drug Resistance of Hybrid Vector | | |
| PNB1 | TET | pSB21 | SP | pNB121 | TET | SP | |
| PNB1 | TET | pSB24 | SP | pNB124 | TET | SP | |
| pSB1 | TET | pSB21 | SP | pSB121 | TET | SP | |
| pSB1 | TET | pSB24 | SP | pSB124 | TET | SP | |
| pSB3 | TET NPT | pSB21 | SP | pSB321 | TET | SP | NPT |
| pSB3 | TET NPT | pSB24 | SP | pSB324 | TET | SP | NPT |
| pSB4 | TET HPT | pSB21 | SP | pSB421 | TET | SP | HPT |
| pSB4 | TET HPT | pSB24 | SP | pSB424 | TET | SP | HPT |

TET: tetracycline resistant; SP: spectinomycin resistant
NPT: kanamycin resistant; HPT: hygromycin resistant By the method of Ditta et al., pGA482, pTOK253 and pGA482-GUS were respectively introduced into LBA4404 to obtain LBA4404(pGA482), LBA4404(pTOK253) and LBA4404(pGA482-GUS).

Example 3

Efficiency of Transformation and Co-transformation of Tobacco

Tobacco (variety: BY4) plants were cultivated in a greenhouse and leaves were collected. The surfaces of the leaves were sterilized with ethanol and sodium hypochlorite and leaf disks with a diameter of about 6 mm were prepared. About $10^8$ cells of one of the following bacteria belonging to the genus Agrobacterium were cultured together with the leaf disk in 2–3 ml of a liquid medium containing inorganic salts of Linsmaier and Skoog's medium and 30 g/l of sucrose for 48 hours.

LBA4404 (pSB324)
LBA4404 (pSB424)
Mixture of equal number of cells of LBA4404(pSB124) and LBA4404(pGA482)

Mixture of equal number of cells of LBA4404(pNB124) and LBA4404(pGA482)

Mixture of equal number of cells of LBA4404(pTOK253) and LBA4404(pGA482)

LBA4404(pGA482-GUS)

LBA4404(pGA482)

After washing each of the leaf disks with sterilized water to remove the bacterial cells, the leaf disks were placed on a medium containing inorganic salts of Linsmaier and Skoog medium, 0.3 mg of indole acetic acid, 10 mg/ml of 6-(γ,γ)-dimethylallylaminopurine, 200 mg/l of kanamycin, 250 mg/ml of cefotaxim and 0.9% of agar. in case of LBA4404 (pSB424), a medium containing 50 mg/l of hygromycin in place of kanamycin was used. After one month from the beginning of the culture, kanamycin resistant or hygromycin resistant plants were examined for expression of GUS by the following method and then cultivated in a greenhouse.

Expression of GUS was examined according to the method of Jefferson et al (Plant Molecular Biology Reporter 5:387–405, 1987) by cutting off small pieces of the leaves (sizing 2×2 mm to 10×10 mm) and immersing the leaf pieces in an aqueous solution containing 500 mg/l 5-bromo-4-chloro-3-indolylglucuronide (X-Gluc), 50 mM sodium phosphate pH 7.0, 10 mM β-mercaptoethanol, 10 mM sodium ethylenediaminetetraacetic acid, 0.1% sodium lauryl sarcosine and 0.1% Triton X-100 for 2 hours to overnight. If the leaf disk exhibits GUS activity, the leaf disk, especially its cross section, is colored in deep blue, and if the leaf disk does not exhibits GUS activity, such coloring is not observed.

The results of examination of GUS expression are as follows.

indicates that by the prior art method, there are cases where no plants which are co-transformed with the two kinds of T-DNA are obtained. This is thought to be a reason why the prior art method is not widely used.

The method in which the mixture of LBA4404(pNB124) and LBA4404(pGA482) is used is a method similar to the above-mentioned prior art by McKnight et al except that a hybrid vector pNB124 is used. By the conventional method of McKnight et al., the second T-DNA was contained in 19% of the drug resistant plants. By the method using the mixture of LBA4404(pNB124) and LBA4404(pGA482), the second T-DNA was contained in 22% of the drug resistant plants. Thus, the result is similar to that of the method of McKnight et al.

As for the method in which the mixture of LBA4404 (pSB124) and LBA4404(pGA482) is used, LBA4404 (pSB124) is a bacterium containing a hybrid vector named pSB124, so that this method utilizes a super binary vector and is the method (two-strain method) according to the present invention. By this method, it was confirmed that the second T-DNA is contained in about 35% of the drug resistant plants. Thus, this method attained much higher co-transformation efficiency than by the method using the mixture of LBA4404(pNB124) and LBA4404(pGA482).

The results of the method using the mixture of LBA4404 (pSB124) and LBA4404(pGA482) and of the method using the mixture of LBA4404(pNB124) and LBA4404(pGA482) may be compared utilizing a statistical analysis as follows.

If a hypothesis that the probabilities of co-transformation by the two methods are the same is employed, $X^2$ is calculated as follows:

$$X^2 = 6.5 \times 6.5 \times (1/28.5 + 1/28.5 + 1/71.5 + 1/71.5) = 4.15$$

TABLE 2

GUS Activity of Transformants

| Agrobacterium Bacterium Used for Transformation | Number of Drug Resistant Plants | Number of Plants Showing GUS Activity | % |
|---|---|---|---|
| LBA4404 (pSB324) | 118 | 61 | 52 |
| LBA4404 (pSB424) | 109 | 54 | 50 |
| Mixture of LBA4404(pSB124) and LBA4404(pGA482) | 100 | 35 | 35 |
| Mixture of LBA4404(pNB124) and LBA4404(pGA482) | 100 | 22 | 22 |
| Mixture of LBA4404(pTOK253) and LBA4404(pGA482) | 110 | 0 | 0 |
| LBA4404 (pGA482-GUS) | 39 | 33 | 85 |
| LBA4404 (pGA482) | 25 | 0 | 0 |

The fact that a plant exhibits drug resistance indicates that the first T-DNA containing the selection marker gene was introduced into the plant and the fact that a plant exhibits GUS activity indicates that the second T-DNA containing the GUS gene was introduced into the plant.

Since LBA4404(pGA482) is a bacterium which does not contain GUS gene, all of the drug resistance plants did not exhibit GUS activity.

Although LBA4404(pGA482-GUS) contains a T-DNA to which the drug resistant gene and GUS gene are ligated, only 85% of the drug resistant plants exhibited GUS activity. This indicates that there are cases wherein the GUS gene may be dropped during the process of transformation, or the GUS activity is not detected because of its insufficient expression even when the GUS gene is introduced.

The method in which the mixture of LBA4404 (pTOK253) and LBA4404(pGA482) is used is the same as the prior art (McKnight et al., Plant Molecular Biology 8:439–445, 1987). By this method, no plants were obtained in which the two kinds of T-DNA were introduced. This This has a degree of freedom of 1. When the degree of freedom is 1, since the probability that $X^2$ is more than 4.15 is not more than 5%, the above-mentioned hypothesis is rejected at a level of 5%. Therefore, the probabilities of the co-transformation by the above-mentioned two methods are statistically significantly different.

The methods utilizing LBA4404(pSB324) or LAB4404 (pSB424) are the methods utilizing a bacterium containing hybrid vector pSB324 and pSB424, respectively. Thus, these methods utilize super binary vectors, and are methods (single-strain method) according to the present invention. By these methods, it was confirmed that the second T-DNA is contained in 50–52% of the drug resistant plants. Thus, it was proved that the efficiency of co-transformation by these methods is much higher than by the method utilizing the mixture of LBA4404(pNB124) and LBA4404(pGA482) or the mixture of LBA4404(pSB124) and LBA4404(pGA482).

The results of the method utilizing LBA4404(pSB324) or LBA4404(pSB424) and the results of the method utilizing the mixture of LBA4404(pSB124) and LBA4404(pGA482) may be compared utilizing a statistical analysis as follows.

If a hypothesis that the probabilities of co-transformation by the two methods are the same is employed, $X^2$ is calculated as follows:

$$X^2=19.9\times19.9\times(1/95.1+1/41.9+1/131.9+1/58.1)=23.43$$

This has a degree of freedom of 1. When the degree of freedom is 1, the probability that $X^2$ is more than 23.43 is not more than 1%, the above-mentioned hypothesis is rejected at a level of 1%. Therefore, the probabilities of the co-transformation by the above-mentioned two methods are statistically significantly different at a level of 1%.

The results of the method utilizing LBA4404(pSB324) or LBA4404(pSB424) and the results of the method utilizing the mixture of LBA4404(pNB124) and LBA4404(pGA482) may be compared utilizing a statistical analysis as follows.

If a hypothesis that the probabilities of co-transformation by the two methods are the same is employed, $X^2$ is calculated as follows:

$$X^2=10.9\times10.9\times(1/104.1+1/45.9+1/122.9+1/54.1)\times6.89$$

This has a degree of freedom of 1. When the degree of freedom is 1, the probability that $X^2$ is more than 6.89 is not more than 1%, the above-mentioned hypothesis is rejected at a level of 1%. Therefore, the probabilities of the co-transformation by the above-mentioned two methods are statistically significantly different at a level of 1%.

Example 4

Inheritance of T-DNA Introduced into Tobacco

Seeds were harvested from transformed plants cultivated in a green house. Seeds from some plants were surface sterilized with ethanol and sodium hypochlorite and then sown on a medium containing inorganic salts of Linsmaier and Skoog, 30 g/l of sucrose and 0.9% of agar. Germinated plants were tested for the GUS activity by the above-mentioned method and for drug resistance by the following method.

Small pieces (about 3 mm×3 mm) were cut off and placed on a medium containing inorganic salts of Linsmaier and Skoog, 30 g/l of sucrose, 3 mg/l of indole acetic acid, 3 mg/l of naphthalene acetic acid, 0.1 mg/l of kinetin, 200 mg/l of kanamycin and 0.9% of agar. Seeds from the plants transformed with LBA4404(pSB424) were placed on the same medium as mentioned above except that 50 mg/l of hygromycin is contained in place of kanamycin. Leaf pieces from drug resistant plants formed calli while leaf pieces from drug sensitive plants died without forming calli.

The results shown in Table 3 below were obtained for the plants originated from the seeds from the plants transformed with LBA4404(pSB324), LBA4404(pSB424) or the mixture of LBA4404(pSB124) and LBA4404(pGA482).

TABLE 3

Segregation of Introduced Drug Resistance and GUS in the Next Generation

| Agrobacterium Bacterium Used for Transformation | Line Number (Individual No. of Transformants of the Present Generation) | Number of Plants | | | |
|---|---|---|---|---|---|
| | | GUS + Resistant | GUS + Sensitive | GUS − Resistant | GUS − Sensitive |
| LBA4404(pSB324) | 324-6 | 45 | 0 | 12 | 4 |
| LBA4404(pSB324) | 324-8 | 7 | 0 | 52 | 0 |
| LBA4404(pSB324) | 324-14 | 49 | 0 | 0 | 11 |
| LBA4404(pSB324) | 324-23 | 37 | 17 | 2 | 0 |
| LBA4404(pSB324) | 324-25 | 49 | 0 | 0 | 11 |
| LBA4404(pSB324) | 324-28 | 35 | 9 | 12 | 3 |
| LBA4404(pSB324) | 324-32 | 0 | 55 | 0 | 4 |
| LBA4404(pSB324) | 324-41 | 16 | 1 | 40 | 3 |
| LBA4404(pSB324) | 324-49 | 42 | 9 | 0 | 4 |
| LBA4404(pSB424) | 424-1 | 32 | 6 | 14 | 6 |
| LBA4404(pSB424) | 424-4 | 30 | 15 | 10 | 4 |
| LBA4404(pSB424) | 424-10 | 50 | 9 | 0 | 1 |
| LBA4404(pSB424) | 424-14 | 55 | 2 | 0 | 0 |
| LBA4404(pSB424) | 424-15 | 45 | 11 | 0 | 1 |
| LBA4404(pSB424) | 424-20 | 48 | 5 | 0 | 1 |
| LBA4404(pSB424) | 424-30 | 39 | 18 | 1 | 1 |
| LBA4404(pSB424) | 424-32 | 55 | 3 | 0 | 0 |
| LBA4404(pSB424) | 424-38 | 39 | 14 | 0 | 6 |
| LBA4404(pSB424) | 424-41 | 26 | 6 | 17 | 5 |
| LBA4404(pSB124)/LBA4404(pGA482) Mixture | 12482-6 | 0 | 0 | 53 | 4 |
| LBA4404(pSB124)/LBA4404(pGA482) Mixture | 12482-9 | 44 | 0 | 13 | 3 |
| LBA4404(pSB124)/LBA4404(pGA482) Mixture | 12482-33 | 21 | 22 | 1 | 16 |
| LBA4404(pSB124)/LBA4404(pGA482) Mixture | 12482-40 | 32 | 0 | 0 | 15 |
| LBA4404(pSB124)/LBA4404(pGA482) Mixture | 12482-53 | 24 | 23 | 0 | 9 |
| LBA4404(pSB124)/LBA4404(pGA482) Mixture | 12482-63 | 38 | 6 | 50 | 0 |
| LBA4404(pSB124)/LBA4404(pGA482) Mixture | 12482-64 | 30 | 5 | 35 | 4 |
| LBA4404(pSB124)/LBA4404(pGA482) Mixture | 12482-66 | 34 | 14 | 13 | 3 |
| LBA4404(pSB124)/LBA4404(pGA482) Mixture | 12482-77 | 84 | 5 | 1 | 1 |
| LBA4404(pSB124)/LBA4404(pGA482) Mixture | 12482-101 | 52 | 0 | 28 | 1 |
| LBA4404(pSB124)/LBA4404(pGA482) Mixture | 12482-108 | 13 | 2 | 72 | 7 |
| LBA4404(PSB124)/LBA4404(pGA482) Mixture | 12482-113 | 57 | 16 | 17 | 5 |
| LBA4404(pSB124)/LBA4404(pGA482) Mixture | 12482-137 | 80 | 18 | 2 | 0 |
| LBA4404(pSB124)/LBA4404(pGA482) Mixture | 12482-139 | 76 | 20 | 0 | 0 |

GUS+: having GUS activity; GUS−: having no GUS activity
Resistant: having drug resistance; Sensitive: having no drug resistance As can be seen from the above-described results, in some cases, more than one T-DNAs containing the drug resistant gene or more than one T-DNAs containing the GUS gene were introduced into the plants.

As for the plants transformed with LBA4404(pSB324), which exhibited GUS activity, with 5 plants among the examined 9 plants, at least one T-DNA containing GUS gene inherited independently from the T-DNA containing the drug resistant gene, and plants containing no drug resistant gene but containing GUS gene were obtained in the next generation.

As for the plants transformed with LBA4404(pSB424), which exhibited GUS activity, with 10 plants among the examined 10 plants, at least one T-DNA containing GUS gene inherited independently from the T-DNA containing the drug resistant gene, and plants containing no drug resistant gene but containing GUS gene were obtained in the next generation.

As for the plants transformed with the mixture of LBA4404(pSB124) and LBA4404(pGA482), which exhibited GUS activity, with 10 plants among the examined 14 plants, at least one T-DNA containing GUS gene inherited independently from the T-DNA containing the drug resistant gene, and plants containing no drug resistant gene but containing GUS gene were obtained in the next generation.

In the next generation of the plants transformed with LBA4404(pGA482-GUS), which exhibited GUS activity, there were no plants which do not contain the drug resistant gene and contain GUS gene. In the next generation of the plants transformed with LBA4404(pGA482), there were no plants which exhibited GUS activity.

From the leaves of the transformants having line Nos. 324-28, 424-4 and 424-30 shown in Table 3, as well as from the leaves of the next generation plants thereof, DNAs were extracted by the method of Komari et al (Theor. Appl. Genet. 77; 547–552, 1989) and digested with restriction enzyme HindIII, followed by Southern analysis according the method of Sambrook et al., (Molecular Cloning: A Laboratory Manual, 2nd Edn. Cold Spring Harbor, N.Y.). As a result, in the plants exhibiting drug resistance and GUS activity, both genes were detected. In the plants which exhibited drug resistance but did not exhibit GUS activity, GUS gene alone was detected. In the plants which did not exhibit drug resistance and GUS activity, none of the genes was detected.

Example 5
Efficiency of Transformation and Co-transformation of Rice

Mature seeds of rice (variety: Tsukinohikari) were immersed in 70% ethanol for 1 minute and then in 1% sodium hypochlorite for 30 minutes to sterilize the seeds, and the sterilized seeds were placed on 2N6 solid medium (inorganic salts and vitamins of N6 (Chu C. C., Proc. Symp. Plant Tissue Culture, Science Press Peking, pp.43–50, 1978), 1 g/l casamino acid, 2 mg/l, 2,4-D, 30 g/l sucrose and 2 g/l Gelrite). After culturing the seed for about 3 weeks, the formed calli originated from scutella were transplanted to 2N6 solid medium, and calli after 4–7 days from the transplantation were employed as scutellum calli.

Colonies of LBA4404(pSB424) obtained by culturing this strain on AB medium at 28° C. for 3–10 days were collected with platinum loop and suspended in modified AA medium (Aa major inorganic salts, AA amino acids and vitamins (Toriyama et al., Plant Science 41:179–183, 1985), MS minor salts (Murashige et al., Physiol. Plant. 15:473–497, 1962), 0.5 g/l of casamino acid, 0.2M of sucrose, 0.2M of glucose, 100 µM of acetosilingone, pH 5.2). After adjusting the cell population to $1 \times 10^9$ cells/ml, the suspension was used for inoculation.

After washing the calli with sterilized water, they were immersed in the above-described cell suspension for 3–10 minutes. After the immersion, the calli were transplanted to 2N6 solid medium containing acetosilingone, glucose and sucrose in the same concentrations as in the modified AA medium, and the calli were cultured in the dark at 25° C. for 3 days. The scutellum calli were then washed with sterilized water containing 250 mg/l of cefotaxime.

The calli were transplanted to 2N6 solid medium containing 250 mg/l hygromycin and 250 mg/l cefotaxime and cultured for 3 weeks, followed by selection of hygromycin resistant calli. The obtained resistant calli were further cultured on N6-7 medium (N6 inorganic salts, N6 vitamins, 2 g/l casamino acid, 1 mg/l 2,4-D, 0.5 mg/l 6BA, 30 g/l sorbitol, 20 g/l sucrose and 2 g/l Gelrite) containing 100 mg/l hygromycin and 250 mg/l cefotaxime for 2–3 weeks. The calli grown on this medium were transplanted to plant regeneration medium N6S3 (½ N6 major inorganic salts, N6 minor salts, N6 vitamins (Chu, 1978), AA amino acids (Toriyama et al., 1985), 1 mg/l casamino acid, 0.2 mg/l naphthalene acetic acid, 1.0 mg/l kinetin and 3 g/l Gelrite) containing 50 mg/l hygromycin and 250 mg/l cefotaxime to regenerate hygromycin resistant plants.

The hygromycin resistant plants were tested for GUS activity by the method described above, and then cultivated in an air-tight green house.

As shown in Table 4 below, hygromycin resistant plants were obtained from 12.3–44.0% of the calli used. Further, as shown in Table 5 below, among the hygromycin resistant plants, 42–51% exhibited GUS activity.

TABLE 4

Efficiency of Selection of Hygromycin Resistant Plants by Co-transformation

| | Number of Calli | | Selection |
| Calli Used (a) | Resistant Calli | Regenerated Calli (b) | Efficiency (b/a: %) |
| --- | --- | --- | --- |
| 227 | 40 | 28 | 12.3 |
| 398 | 90 | 75 | 18.8 |
| 220 | 116 | 97 | 44.0 |
| 324 | 77 | 72 | 22.2 |

TABLE 5

GUS Activity in Hygromycin Resistant Plants

| Number of Drug Resistant Plants Used | Number of Plants Exhibiting GUS Activity | % |
| --- | --- | --- |
| 97 | 41 | 42 |
| 176 | 82 | 47 |
| 126 | 60 | 48 |
| 150 | 76 | 51 |

From the leaves of the plants which exhibited hygromycin resistance and GUS activity, DNAs were extracted by the method of Komari et al (Theor. Appl. Genet. 77; 547–552, 1989) and digested with restriction enzyme HindIII, followed by Southern analysis according the method of Sambrook et al., (Molecular Cloning: A Laboratory Manual, 2nd Edn. Cold Spring Harbor, N.Y.). As a result, in all of the plants, the existence of hygromycin resistant gene and GUS gene were confirmed (Table 6).

TABLE 6

Results of Southern Analysis of Transformants and Segregation of Introduced Gene in the Next Generation

| Line of Transformant | Southern Analysis Number of Copies of Introduced Gene | | Number of Plants in the Next Generation | | | |
|---|---|---|---|---|---|---|
| | HPT* | GUS | GUS + Resistant | GUS + Sensitive | GUS – Resistant | GUS – Sensitive |
| 1 | 1 | 1 | 44 | 11 | 12 | 3 |
| 2 | 1–2 | 2–3 | 41 | 22 | 2 | 5 |
| 3 | 2–3 | 2–3 | 67 | 1 | 2 | 0 |
| 4 | 4 | 2 | 68 | 2 | 6 | 0 |
| 5 | 1 | 2 | 51 | 14 | 0 | 5 |
| 6 | 2 | 1 | 52 | 0 | 0 | 18 |
| 7 | 1 | 1 | 51 | 0 | 0 | 19 |
| 8 | 1 | 2 | 34 | 11 | 17 | 7 |
| 9 | 2 | 3–4 | 14 | 43 | 4 | 9 |
| 10 | 2 | 1 | 52 | 0 | 14 | 3 |
| 11 | 1 | 2–3 | 46 | 17 | 0 | 7 |
| 12 | 2 | 2 | 51 | 0 | 0 | 19 |

*HPT: hygromycin resistant gene

Example 6
Inheritance of T-DNA Introduced into Rice

Seeds were harvested from transformed plants cultivated in a green house. Seeds from some plants were surface sterilized with ethanol and sodium hypochlorite and then sown on a medium containing no N6 hormones. Germinated and rooted seeds were tested for the GUS activity by the method described above and for hygromycin resistance by the method as follows.

Radicles were cut to a length of 5–10 mm and the obtained radicle fragments were placed on 2N6 medium containing 50 mg/l of hygromycin. The radicle fragments from hygromycin resistant plants formed calli while those from hygromycin sensitive plants died without forming calli.

The results shown in Table 6 were obtained for the next generation plants originated from the seeds of the plants which were transformed with LBA4404(pSB424) and exhibited GUS activity and hygromycin resistance.

As can be seen from the results, in some of these plants, like tobacco plants, multiple T-DNAs containing the drug resistant gene or multiple T-DNAs containing the GUS gene were introduced. The number of genes was the same as, or smaller than the number of copies detected by Southern analysis. In cases where the number of genes is smaller than the number of copies detected by Southern analysis, it is thought that multiple copies of genes were introduced into the same locus.

As for the plants transformed with LBA4404(pBS424), which exhibited GUS activity and hygromycin resistance, with 8 plants among the examined 12 plants, the T-DNA containing at least one GUS gene inherited independently from the T-DNA containing the drug resistant gene, and plants containing no drug resistant gene but containing GUS gene were obtained in the next generation.

To confirm the existence of the introduced genes in the next generation plants of the transformed plants, the next generation plants of the plants of each line shown in Table 6 were classified according to the phenotypes (GUS+ and hygromycin resistant, GUS+ and hygromycin sensitive, GUS– and hygromycin resistant, and GUS– and hygromycin sensitive) and subjected to Southern analysis. As a result, it was confirmed that the existence of hygromycin resistant gene and GU$ gene was coincident with the phenotype.

Industrial Availability

As described above, the present invention made it possible to prepare transformed and regenerated plants into which a desired gene is introduced at a high efficiency, and to obtain in the next generation the plants which contain the desired gene but not contain the drug resistant gene used as a selection marker. Thus, the present invention is useful for creating a novel useful plant having the desired character, so that the present invention is useful in agriculture.

What is claimed is:

1. A method for transforming and cultivating a plant using a bacterium belonging to the genus Agrobacterium, comprising:

co-transforming plant cells with a first T-DNA (1) and a second T-DNA (2); and selecting cells based on a selection marker gene;

said first T-DNA (1) containing a selection marker gene which functions in said plant;

said second T-DNA (2) containing a desired DNA fragment to be introduced into said plant, the second T-DNA (2) being contained in a hybrid vector;

said hybrid vector being prepared by homologous recombination between an acceptor vector and an intermediate vector in said bacterium belonging to the genus Agrobacterium;

said acceptor vector containing at least
   (a) a DNA region having a replication origin allowing replication of a plasmid in both a bacterium belonging to the genus Agrobacterium and in *Escherichia coli*,
   (b) a DNA region containing virB gene and virG gene in virulence region of Ti plasmid pTiBo542 of *Agrobacterium tumefaciens*, and
   (c) a DNA region which is homologous with a part of said intermediate vector, which is subjected to homologous recombination in said bacterium belonging to the genus Agrobacterium;

said intermediate vector containing at least
   (i) a DNA region having a replication origin allowing replication of a plasmid in *Escherichia coli*, which does not function in said bacterium belonging to the genus Agrobacterium, (ii) a DNA region which is homologous with a part of said acceptor vector, which is subjected to homologous recombination in said bacterium belonging to the genus Agrobacterium, and (iii) a DNA region which constitutes at least a part of said second T-DNA;

obtaining a plant transformed with said selection marker gene and said desired DNA fragment; and cultivating said plant and selecting a plant in the next generation, which contains said desired DNA fragment but does not contain said selection marker gene.

2. The method according to claim 1, wherein said selection marker gene is a gene giving drug resistance.

3. The method according to claim 1 or 2, wherein said first T-DNA is contained in said hybrid vector with said second T-DNA.

4. The method according to claim 3, wherein said first T-DNA is contained in said acceptor vector.

5. The method according to claim 1, wherein said first T-DNA and said second T-DNA are separated on said hybrid vector by (1) said DNA region having a replication origin allowing replication of a plasmid in both a bacterium belonging to the genus Agrobacterium and in *Escherichia coli*, and (2) said DNA region containing virB gene and virG gene in virulence region of Ti plasmid pTiBo542 of *Agrobacterium tumefaciens*.

6. The method according to claim 1 or 2, wherein said first T-DNA and said hybrid vector are contained in different Agrobacterium bacterial cells and said plant is transformed with a mixture of these two types of Agrobacterium cells.

7. The method according to claim 6, wherein said T-DNA is contained in a vector which does not contain the virB and virG regions of the virulence region of the Ti plasmid pTiBo542 of *Agrobacterium tumefaciens*.

8. The method according to claim 1, wherein said desired DNA region containing virB gene and virG gene in virulence region of Ti plasmid pTiBo542 of *Agrobacterium tumefaciens* is Kpn I fragment having a size of 15.2 kb of pTiBo542.

9. The method according to claim 1 or 2, wherein said desired DNA fragment to be introduced into said plant is inserted into said DNA region constituting at least a part of said second T-DNA utilizing a restriction site.

10. The method according to claim 1 or 2, wherein said intermediate vector contains the entire region of said second T-DNA.

11. The method according to any one of claim 1 or 2, wherein a bacterium belonging to the genus Agrobacterium containing said hybrid vector together with a Ti plasmid or Ri plasmid which does not contain T-DNA but contains a virulence region needed for transfer of T-DNA to a plant, is infected to said plant.

12. The method according to claim 2, wherein said gene giving said drug resistance is kanamycin resistant gene or hygromycin resistant gene.

13. The method according to claim 6, wherein said first T-DNA is located on a plasmid, and a bacterium belonging to the genus Agrobacterium containing said first T-DNA together with a second plasmid originated from Ti plasmid or Ri plasmid containing the virulence region needed for transfer of T-DNA to said plant but not containing a T-DNA, is infected to said plant.

14. The method according to claim 1 or 2, wherein said acceptor vector is pSB3 or pSB4.

15. The method according to claim 1, wherein said intermediate vector is pSB21, pSB22, pSB24, pTOK170; pYS151, pTOK235, pTOK245 or pTK246.

16. A hybrid vector comprising:

a first T-DNA containing (1) a selection marker gene which functions in a plant, and (2) a second T-DNA having a restriction site;

wherein there is sufficient distance on said hybrid vector between said first T-DNA and said second T-DNA to allow said first T-DNA and second T-DNA to be independently inherited, said hybrid vector being prepared by homologous recombination between an acceptor vector and an intermediate vector in a bacterium belonging to the genus Agrobacterium;

said acceptor vector containing at least (a) a DNA region having a replication origin allowing replication of a plasmid in both a bacterium belonging to the genus Agrobacterium and in *Escherichia coli*, (b) a DNA region containing virB gene and virG gene in virulence region of Ti plasmid pTiBo542 of *Agrobacterium tumefaciens*, and (c) a DNA region which is homologous with a part of said intermediate vector, which is subjected to homologous recombination in said bacterium belonging to the genus Agrobacterium;

said intermediate vector containing at least (i) a DNA region having a replication origin allowing replication of a plasmid in *Escherichia coli*, which does not function in said bacterium belonging to the genus Agrobacterium, (ii) a DNA region which is homologous with a part of said acceptor vector, which is subjected to homologous recombination in said bacterium belonging to the genus Agrobacterium, and (iii) a DNA region which constitutes at least a part of said second T-DNA.

17. The hybrid vector according to claim 16, wherein said selection marker gene is a gene giving drug resistance.

18. The hybrid vector according to claim 16 or 17, wherein said first T-DNA is contained in said acceptor vector.

19. The hybrid vector according to claim 16, wherein said first T-DNA and said second T-DNA are separated on said hybrid vector by (1) said DNA region having a replication origin allowing replication of a plasmid in both a bacterium belonging to the genus Agrobacterium and in *Escherichia coli*, and (2) said DNA region containing virB gene and virG gene in virulence region of Ti plasmid pTiBo542 of *Agrobacterium tumefaciens*.

20. The hybrid vector according to claim 16, wherein said DNA region containing virB gene and virG gene in virulence region of Ti plasmid pTiBo542 of *Agrobacterium tumefaciens* is Kpn I fragment having a size of 15.2 kb of pTiBo542.

21. The hybrid vector according to claim 17, wherein said gene giving said drug resistance is kanamycin resistant gene or hygromycin resistant gene.

22. The hybrid vector according to claim 16 or 17, wherein said acceptor vector is pSB3 or pSB4.

23. The hybrid vector according to claim 16 or 17, wherein said intermediate vector is pSB21, pSB22, pSB24, pTOK170, pYS151, pTOK235, pTOK245 or pTOK246.

24. A method for transforming and cultivating a plant using a bacterium belonging to the genus Agrobacterium, comprising co-transforming plant cells with a first T-DNA (1) and a second T-DNA (2); and selecting the cells which acquired drug resistance;

said first T-DNA (1) containing a gene giving said drug resistance, which functions in said plant;

said second T-DNA (2) containing a desired DNA fragment to be introduced into said plant, the second T-DNA (2) being contained in a hybrid vector;

said hybrid vector being prepared by homologous recombination between an acceptor vector and an intermediate vector in said bacterium belonging to the genus Agrobacterium;

said acceptor vector being pSB3 or pSB4; and said intermediate vector being pSB21, pSB22, pSB24, pTOK170, pYS151, pTOK235, pTOK245 or pTOK246;

obtaining a plant transformed with said drug resistance gene and said desired DNA fragment; and cultivating said plant and selecting a plant in the next generation, which contains said desired DNA fragment but does not contain said drug resistance gene.

25. A hybrid vector comprising:

a first T-DNA containing (1) a gene giving a drug resistance, which functions in a plant; and (2) a second T-DNA having a restriction site; wherein there is sufficient distance on said hybrid vector between said first T-DNA and said second T-DNA to allow said first T-DNA and said second T-DNA to be independently inherited.

said hybrid vector being prepared by homologous recombination between an acceptor vector and an intermediate vector in a bacterium belonging to the genus Agrobacterium;

said acceptor vector being pSB3 or pSB4; and said intermediate vector being pSB21, pSB22, pSB24, pTOK170, pYS151, pTOK235, pTOK245 or pTOK246.

* * * * *